US006797860B2

(12) United States Patent
Sakagami et al.

(10) Patent No.: US 6,797,860 B2
(45) Date of Patent: Sep. 28, 2004

(54) PROMOTER DERIVED FROM PHYTOSULFOKINE PRECURSOR GENE

(75) Inventors: Yoji Sakagami, Nagoya (JP); Heping Yang, Nagoya (JP); Yoshikatsu Matsubayashi, Nagoya (JP)

(73) Assignee: Nagoya University, Nagoya (JP)

( * ) Notice: Subject to any disclaimer, the term of this patent is extended or adjusted under 35 U.S.C. 154(b) by 0 days.

(21) Appl. No.: 09/880,006

(22) Filed: Jun. 14, 2001

(65) Prior Publication Data

US 2002/0103363 A1 Aug. 1, 2002

(30) Foreign Application Priority Data

Jun. 15, 2000 (JP) ....................................... 2000-179826

(51) Int. Cl.[7] ......................... C12N 15/11; C12N 15/79; C12N 15/82; C12N 5/04; A01H 5/00

(52) U.S. Cl. ...................... 800/298; 800/278; 536/23.1; 536/24.1; 435/320.1; 435/419

(58) Field of Search .............................. 435/419, 320.1, 435/410, 468; 800/278, 295, 298; 536/23.1, 24.1

(56) References Cited

FOREIGN PATENT DOCUMENTS

FR 2 791 347 A 9/2000

OTHER PUBLICATIONS

Fourgoux–Nicol A. et al. 1999, Plant Molecular Biology vol. 40: pp. 857–872.*

Benfey P. et al., Science 250:959–966, 1990.*

Park Y. D. et al., Plant Journal 1996, Feb. 9, (2): 183–194.*

Yang H. et al. GenBank Accession No. AB026837 submitted Apr. 28, 1999.*

Christensen A. et al. Transgenic Research, 1996, vol. 5 pp. 213–218.*

Yang, H., et al., "Oryza sativa PSK gene encodes a precursor of phytosulfokine–aplha, a sulfated peptide growth factor found in plants." Proceedings of the National Academy of Sciences of USA, National Academy of Science, Washington, D.C., vol. 96, No. 23, (Nov. 9, 1999), pp. 13560–13565. XP002175646.

Yang, H., et al., "Molecular cloning and characterization of *OdPSK*, a gene encoding a precursor for phytosulfokine –α, required for rice cell proliferation." Plant Molecular Biology, vol. 44, No. 5 (Nov. 2000), pp , 635–647. XP001015809.

Database Embl Online! AB020505 (Nov. 12, 1999), Yang, H., et al., "Oryza sativa OsPSK gene for preprophytosulfokine." XP002182544.

Database Embl Online! AB026837 (Dec. 21, 2000), Yang, H., et al., "Oryza sativa OsPSK gene for preprophytosulfokine." XP002182545.

Database Embl Online! AQ290662 (Dec. 3, 1998), Wing, R.A., et al., "A BAC end sequencing framework to sequence the rice genome." XP002182546.

* cited by examiner

*Primary Examiner*—David T. Fox
*Assistant Examiner*—Russell Kallis
(74) *Attorney, Agent, or Firm*—Burns, Doane, Swecker & Mathis, L.L.P.

(57) ABSTRACT

This invention provides a novel promoter derived from gene of phytosulfokine precursor derived from rice. The novel promoter of this invention can enhance expression of an exogenous structural gene with higher potency compared with conventional cauliflower mozaic virus 35S promoter.

13 Claims, 10 Drawing Sheets gaattcctggtttagttttctattagttgggcacaagatcataactgcagtattgtatttaagattcaacacaggttcaatttgtcacaccctgtaattt -3260
↑ -3359
ggcatctacaatctgaaaatgaatggctaatcaaaggctctgagcacacaaatggctaatttcttccatctagttgagaaacctttcaattatacaaat -3160 ggaaaagatatggatgtgatttgtgggctgaaaccctttgataatcaacaattgttagtgccttcaactttcaatgcacccatgttttcttgttacgtt -3060 tgcaagatcaaaacaatgttggaaacgtcatctcgccaggtaaagcaatgaatgacgacaattaagaagattttgctcctgaagactactaatgatgga -2960 tattaagggtataataacctatccaggattgtgatgttcaatccccttgtagcatacctgataagtgtggtgagttaaaagcagtcccatttacaaaaag -2860 aaaaaggaaggcccatatctagcaaaaaaaatagactgcatacgtatagttgtttgtgaaaaagttcaagatgcatacaagccgcagttttcttcagata -2760 gtgtggcatcttcttacttcaaggaaaaaaacattatgctagtttggaaataacttcaaatttgtccctgtgatggaaattaaaccattggtaagtagtc -2660 tagcaatatcaaacttaaggtgtgtgttgcatatgaattaggaaaaaccatgtcaaac<u>caactg</u>aaaccaaggaaaatccaccatactaacatacttaaa -2560
E box taccttgaggtgagaaacatataaagcatacagagaacatgattagtaagaatgacgaagataaaatacactaaggtaattagggaaaacagcaaagttc -2460 atttggacatttgatatcatggaaagctatagaaaaatgtgtaccttacagaccgaaatggaaagagtccacgataaaaagtcattttgcaccattttc -2360 cattgtaatacttatcgagacaaatttatgcgcgcaccttttttcccccatccatccaaataaattttattggtaaaacttgttgctttatgacagcag -2260 gaagtatcttttacaatctaatgtacccatcagtacaatattctagtagtatatctacaacaaaaataaagatcaagggcatgcttggcacatagaattt -2160 tgtatggaattagttcaagtcatttgttaagcacataaatttggcaaaactctcatcttccaaattaaccttgcaaaatttaaccaagaaaaactatata -2060

FIG. 4A ctatcatcccgttccatgtccttcctagtagcaaactttttatgcaaccatttttttttctcgacagggcattattcgtggttactgtgtgcattaatag -1960 cattaataacagctagcatgtgagcctgttattaggggtaggcagaaagatctgaaccgaaaagaccgacaccgagtaaatttggtcatcaattcggtcc -1860

E box ↑ -1911 tatatagtgaaagaccgaactttattcggtcaattcggttagtctcctcggttaaccgaatagacgaaagaccaaattaacaaaaaaaaaatctaaatgc -1760 aacctacaatccaccaagttcaatataattaaactctaattttcacagccctacttcttctaggcatgcaacgtaataagagtctttagtcatacgtgct -1660 tatggatttgttttgtgatttttgtgttaaaaatttccattatttctttgcatatatgaaaatgttgctgaatttcggtcagaccgagaccgagaccgaa -1560

SSRE SSRE tttgtcggtcatgatatttttttgcgttgaaatttggtctttacttttcgaagatcgagaccgaatatttcggtcagaccgaatgcccacccctacttgtt -1460

SSRE ctctctatacccatatgtcaataataattattattatactcactccgttctaaactatgaggcacttccttttaatgaaaaatcaaactcgataacttt -1360 taattaaaaataatactaatatatactaaatattatgcatgttatatcactatatttatattttaaagtactttcatgtaatgctaatttcatattcgtt -1260 aaaatatagatattataattcaagatggaggagtacaaccaaacagtagaggatccacttcctctttatttatgccaagttattttagaaccatgctcca -1160 cacaagacacgcacacatcgcattgacatgtgttaattttgtttcgtgtggaaaggcatggaggccggttccccacaatgtccaatcgctgccaactctg -1060

E box Enhancer core CCAAT box cgagtagagaagggggaggaatggaagcttgtgcatggcctaaacacacactttgacacttgactttgtgttggaatccattgattagccgctcaatgca -960

↑ -1034 *Binding site for SEF3* gcatccccaatgcagaggtctcccctctactcctagctctttgcaaaacccaatgtccaccattgacttcaatttctcagtcttccttgctcatgtctcc -860

CCAAT box CCAAT box cttgcccttctctcaacttgggtcaacttcattaaatttctcccttggtatgtgcaaaggctttgaaggtgtaggcctggtgcaaacattgcaaagtcaa -760

FIG. 4B

```
aatgtacggtacgatgcatcgatttactgacatggtaatcttcccgattcccgtgtaaataaactactatttcattcgtttcatttataagatgttttaa  -660

ttttgttatgggccaaaacttgcttaactttgacatagtttattgaaaaaaaataggttagaaacttaaattcaggaaaaaaagataggtgagatatcc  -560
                                                                                             ↑-563
tagtataaccatcttggtttggttaagacatgccttagaatagacgagtcggtcgaaacggtcagaatcggtagcgtccctttagaaacgacgctcaatc  -460

gacctgtaattgaccgtatttatcatttacaacattaatacaatgcaaaaagaaattagaaatttttttataaatagtcaaaaatggtacgccagtctat  -360

cgggaatttatgtgaccgttttcacccctattcgagtgcatgggcacttgagttgtaaaattgacttgatcgagataccaacgtatatacaatttacaca  -260
                                                                                      CAAT box
tcgaattgccgggaaattggactttgagatcattttagctccccaaggcgatccacacgtactctaccacaaaactttggttgtttttgctatcatctca  -160

aggccactgcagcatgcgcattgcgcacgtacgagatgctactctttccaaggaaccgatgtctctctctctctccagcctccattgcttataaatat    -60
         ↑ -148                                         +1                                TATA box
gttcctccttcctatactggtaatggcagcaaagcaaagaaacaaagaagaagaagaaaGAAGAAGCAGCAGCAAAAAAGTTGATCAGTTAATTAGCAAG    41

TGTGTTCTTCTTTCTTTTGGTGAGAGAGAGAGAGAGAGAGAGAGAGAGAGAGATCTCAGAATGGTGAATCCAGGAAGAACAGCTAGGGCACTCTGCCTCC   141
                                                           M  V  N  P  G  R  T  A  R  A  L  C  L  L
TATGCCTTGCTCTCCTCCTGCTAGGTCAAGATACCCATTCCAGGAAGCTCCTGTTGCAGGAGAAGCACAGCCATGGCGTCGGCAACGGCACAACCACCAC   241
 C  L  A  L  L  L  L  G  Q  D  T  H  S  R  K  L  L  L  Q  E  K  H  S  H  G  V  G  N  G  T  T  T  T
CCAGGtcagcagaattagttcagtatcgtttcttcagcttattaaccgtggccaaatttgaattctataacttaattttagagttgatgtggatgtgtta   341
 Q
ttaatcatagattatttctcaacattgggttttatgccgctaataacacatatgtaaaacctttacaaacaaattatttttcggtcgctaataagcgtta   441
cggcttataattttcctagtgaacagtgcatgcattttgcaaacttcttgttggctctggttgcaacttgcaagcacgcatatgcattgagagaagagtt   541
```

FIG. 4C

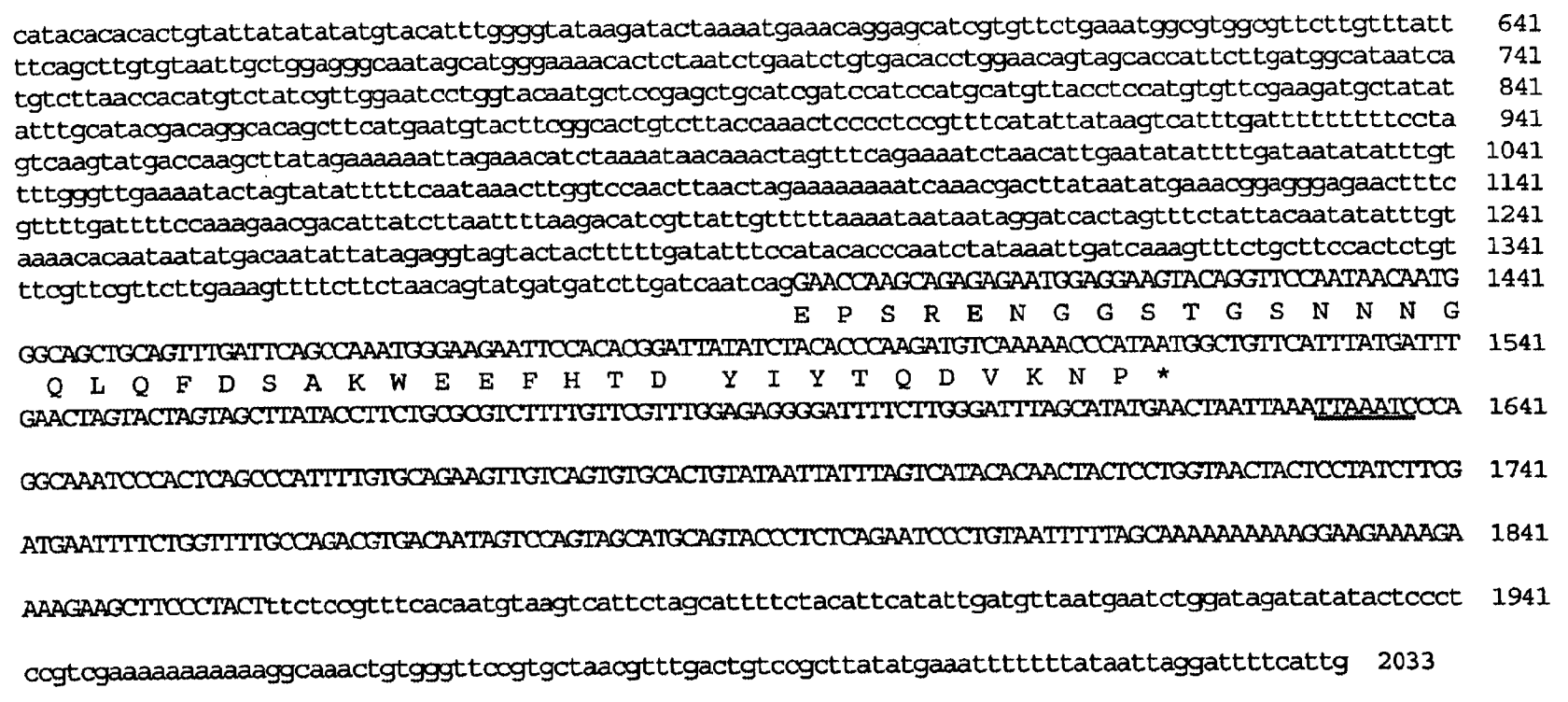

```
catacacacactgtattatatatatgtacatttggggtataagatactaaaatgaaacaggagcatcgtgttctgaaatggcgtggcgttcttgtttatt   641
ttcagcttgtgtaattgctggagggcaatagcatgggaaaacactctaatctgaatctgtgacacctggaacagtagcaccattcttgatggcataatca   741
tgtcttaaccacatgtctatcgttggaatcctggtacaatgctccgagctgcatcgatccatccatgcatgttacctccatgtgttcgaagatgctatat   841
atttgcatacgacaggcacagcttcatgaatgtacttcggcactgtcttaccaaactcccctccgtttcatattataagtcatttgatttttttttccta   941
gtcaagtatgaccaagcttatagaaaaaattagaaacatctaaaataacaaactagtttcagaaaatctaacattgaatatattttgataatatatttgt  1041
tttgggttgaaaatactagtatattttcaataaacttggtccaacttaactagaaaaaaaatcaaacgacttataatatgaaacggagggagaactttc  1141
gttttgattttccaaagaacgacattatcttaatttaagacatcgttattgtttttaaaataataataggatcactagtttctattacaatatatttgt  1241
aaaacacaataatatgacaatattatagaggtagtactacttttgatatttccatacacccaatctataaattgatcaaagtttctgcttccactctgt  1341
ttcgttcgttcttgaaagttttcttctaacagtatgatgatcttgatcaatcagGAACCAAGCAGAGAGAATGGAGGAAGTACAGGTTCCAATAACAATG  1441
                                                        E  P  S  R  E  N  G  G  S  T  G  S  N  N  N  G
GGCAGCTGCAGTTTGATTCAGCCAAATGGGAAGAATTCCACACGGATTATATCTACACCCAAGATGTCAAAAACCCATAATGGCTGTTCATTTATGATTT  1541
 Q  L  Q  F  D  S  A  K  W  E  E  F  H  T  D   Y  I  Y  T  Q  D  V  K  N  P  *
GAACTAGTACTAGTAGCTTATACCTTCTGCGCGTCTTTTGTTCGTTTGGAGAGGGGATTTTCTTGGGATTTAGCATATGAACTAATTAAATTAAATCCCA  1641

GGCAAATCCCACTCAGCCCATTTTGTGCAGAAGTTGTCAGTGTGCACTGTATAATTATTTAGTCATACACAACTACTCCTGGTAACTACTCCTATCTTCG  1741

ATGAATTTTCTGGTTTTGCCAGACGTGACAATAGTCCAGTAGCATGCAGTACCCTCTCAGAATCCCTGTAATTTTTAGCAAAAAAAAAAGGAAGAAAAGA  1841

AAAGAAGCTTCCCTACTttctccgtttcacaatgtaagtcattctagcattttctacattcatattgatgttaatgaatctggatagatatatactccct  1941

ccgtcgaaaaaaaaaaaggcaaactgtgggttccgtgctaacgtttgactgtccgcttatatgaaatttttttataattaggattttcattg  2033
```

FIG. 4D

SEQUENCE LISTING

<160> NUMBER OF SEQ ID NOS: 6

<210> SEQ ID NO 1
<211> LENGTH: 3359
<212> TYPE: DNA
<213> ORGANISM: Oryza sativa L. Oc cell

<400> SEQUENCE: 1
gaattcctgg tttagttttc tattagttgg gcacaagatc ataactgcag tattgtattt 60
aagattcaac acaggttcaa tttgtcacac cctgtaattt ggcatctaca atctgaaaat 120
gaatggctaa tcaaaaggct ctgagcacac aaatggctaa tttcttccat ctagttgaga 180
aacctttcaa ttatacaaat ggaaaagata tggatgtgat ttgtgggctg aaaacccttt 240
gataatcaac aattgttagt gccttcaact ttcaatgcac ccatgttttc ttgttacgtt 300
tgcaagatca aaacaatgtt ggaaacgtca tctcgccagg taaagcaatg aatgacgaca 360
attaagaaga tttttgctcc tgaagactac taatgatgga tattaagggt ataataacct 420
atccaggatt gtgatgttca atccccttgt agcatacctg ataagtgtgg tgagttaaaa 480
gcagtcccat ttacaaaaag aaaaaggaag gcccatatct agcaaaaaaa atagactgca 540
tacgtatagt tgtttgtgaa aaagttcaag atgcatacaa gccgcagttt tcttcagata 600
gtgtggcatc ttcttacttc aaggaaaaaa acattatgct agtttggaaa taacttcaaa 660
tttgtccctg tgatggaaat taaaccattg gtaagtagtc tagcaatatc aaacttaagg 720
tgtgtgttgc atatgaatta ggaaaaacca tgtcaaacca actgaaacca aggaaaatcc 780
accatactaa catacttaaa taccttgagg tgagaaacat ataaagcata cagagaacat 840
gattagtaag aatgacgaag ataaaataca ctaaggtaat tagggaaaac agcaaagttc 900
atttggacat ttgatatcat ggaaagctat agaaaaatgt gtaccttaca gaccgaaatg 960
gaaagagtcc acgataaaaa gtcatttttg caccattttc cattgtaata cttatcgaga 1020
caaatttatg cgcgcacctt ttttccccca tccatccaaa taaattttta ttggtaaaac 1080
ttgttgcttt atgacagcag gaagtatctt ttacaatcta atgtacccat cagtacaata 1140
ttctagtagt atatctacaa caaaaataaa gatcaagggc atgcttggca catagaattt 1200
tgtatggaat tagttcaagt catttgttaa gcacataaat ttggcaaaac tctcatcttc 1260
caaattaacc ttgcaaaatt taaccaagaa aaactatata ctatcatccc gttccatgtc 1320
cttcctagta gcaaactttt tatgcaacca tttttttttc tcgacagggc attattcgtg 1380
gttactgtgt gcattaatag cattaataac agctagcatg tgagcctgtt attaggggta 1440
ggcagaaaga tctgaaccga aaagaccgac accgagtaaa tttggtcatc aattcggtcc 1500
tatatagtga aagaccgaac tttattcggt caattcggtt agtctcctcg gttaaccgaa 1560
tagacgaaag accaaattaa caaaaaaaaa atctaaatgc aacctacaat ccaccaagtt 1620
caatataatt aaactctaat tttcacagcc ctacttcttc taggcatgca acgtaataag 1680
agtctttagt catacgtgct tatggatttg ttttgtgatt tttgtgttaa aaatttccat 1740
tatttctttg catatatgaa aatgttgctg aatttcggtc agaccgagac cgagaccgaa 1800
tttgtcggtc atgatatttt ttgcgttgaa atttggtctt tacttttcga agatcgagac 1860
cgaatatttc ggtcagaccg aatgcccacc cctacttgtt ctctctatac ccatatgtca 1920
ataataatta ttattatact cactccgttc taaactatga ggcacttcct ttttaatgaa 1980
aaatcaaact cgataacttt taattaaaaa taatactaat atatactaaa tattatgcat 2040

-continued

```
gttatatcac tatatttata ttttaaagta ctttcatgta atgctaattt catattcgtt   2100
aaaatataga tattataatt caagatggag gagtacaacc aaacagtaga ggatccactt   2160
cctctttatt tatgccaagt tattttagaa ccatgctcca cacaagacac gcacacatcg   2220
cattgacatg tgttaatttt gtttcgtgtg gaaaggcatg gaggccggtt ccccacaatg   2280
tccaatcgct gccaactctg cgagtagaga agggggagga atggaagctt gtgcatggcc   2340
taaacacaca ctttgacact tgactttgtg ttggaatcca ttgattagcc gctcaatgca   2400
gcatccccaa tgcagaggtc tcccctctac tcctagctct ttgcaaaacc caatgtccac   2460
cattgacttc aatttctcag tcttccttgc tcatgtctcc cttgcccttc tctcaacttg   2520
ggtcaacttc attaaatttc tcccttggta tgtgcaaagg ctttgaaggt gtaggcctgg   2580
tgcaaacatt gcaaagtcaa aatgtacggt acgatgcatc gatttactga catggtaatc   2640
ttcccgattc ccgtgtaaat aaactactat ttcattcgtt tcatttataa gatgttttaa   2700
ttttgttatg ggccaaaact tgcttaactt tgacatagtt tattgaaaaa aaataggtta   2760
gaaaacttaa attcaggaaa aaaagatagg tgagatatcc tagtataacc atcttggttt   2820
ggttaagaca tgccttagaa tagacgagtc ggtcgaaacg gtcagaatcg gtagcgtccc   2880
tttagaaacg acgctcaatc gacctgtaat tgaccgtatt tatcatttac aacattaata   2940
caatgcaaaa agaaattaga aatttttttta taaatagtca aaaatggtac gccagtctat   3000
cgggaattta tgtgaccgtt ttcaccccta ttcgagtgca tgggcacttg agttgtaaaa   3060
ttgacttgat cgagatacca acgtatatac aatttacaca tcgaattgcc gggaaattgg   3120
actttgagat cattttagct ccccaaggcg atccacacgt actctaccac aaaactttgg   3180
ttgtttttgc tatcatctca aggccactgc agcatgcgca ttgcgcacgt acgagatgct   3240
actctttcca aggaaccgat gtctctctct ctctctccag cctccattgc ttataaatat   3300
gttcctcctt cctatactgg taatggcagc aaagcaaaga aacaaagaag aagaagaaa    3359
```

<210> SEQ ID NO 2
<211> LENGTH: 1911
<212> TYPE: DNA
<213> ORGANISM: Oryza sativa L. Oc cell

<400> SEQUENCE: 2

```
gatctgaacc gaaaagaccg acaccgagta aatttggtca tcaattcggt cctatatagt     60
gaaagaccga actttattcg gtcaattcgg ttagtctcct cggttaaccg aatagacgaa    120
agaccaaatt aacaaaaaaa aaatctaaat gcaacctaca atccaccaag ttcaatataa    180
ttaaactcta attttcacag ccctacttct tctaggcatg caacgtaata agagtcttta    240
gtcatacgtg cttatggatt tgttttgtga tttttgtgtt aaaaatttcc attatttctt    300
tgcatatatg aaaatgttgc tgaatttcgg tcagaccgag accgagaccg aatttgtcgg    360
tcatgatatt ttttgcgttg aaatttggtc tttacttttc gaagatcgag accgaatatt    420
tcggtcagac cgaatgccca cccctacttg ttctctctat acccatatgt caataataat    480
tattattata ctcactccgt tctaaactat gaggcacttc ctttttaatg aaaaatcaaa    540
ctcgataact tttaattaaa aataatacta atatatacta aatattatgc atgttatatc    600
actatattta tattttaaag tactttcatg taatgctaat ttcatattcg ttaaaatata    660
gatattataa ttcaagatgg aggagtacaa ccaaacagta gaggatccac ttcctcttta    720
tttatgccaa gttattttag aaccatgctc cacacaagac acgcacacat cgcattgaca    780
```

-continued

```
tgtgttaatt ttgtttcgtg tggaaaggca tggaggccgg ttccccacaa tgtccaatcg    840

ctgccaactc tgcgagtaga gaagggggag gaatggaagc ttgtgcatgg cctaaacaca    900

cactttgaca cttgactttg tgttggaatc cattgattag ccgctcaatg cagcatcccc    960

aatgcagagg tctcccctct actcctagct ctttgcaaaa cccaatgtcc accattgact   1020

tcaatttctc agtcttcctt gctcatgtct cccttgccct tctctcaact tgggtcaact   1080

tcattaaatt tctcccttgg tatgtgcaaa ggctttgaag gtgtaggcct ggtgcaaaca   1140

ttgcaaagtc aaaatgtacg gtacgatgca tcgatttact gacatggtaa tcttcccgat   1200

tcccgtgtaa ataaactact atttcattcg tttcatttat aagatgtttt aattttgtta   1260

tgggccaaaa cttgcttaac tttgacatag tttattgaaa aaaaataggt tagaaaactt   1320

aaattcagga aaaaaagata ggtgagatat cctagtataa ccatcttggt ttggttaaga   1380

catgccttag aatagacgag tcggtcgaaa cggtcagaat cggtagcgtc cctttagaaa   1440

cgacgctcaa tcgacctgta attgaccgta tttatcattt acaacattaa tacaatgcaa   1500

aaagaaatta gaaatttttt tataaatagt caaaaatggt acgccagtct atcgggaatt   1560

tatgtgaccg ttttcacccc tattcgagtg catgggcact tgagttgtaa aattgacttg   1620

atcgagatac caacgtatat acaatttaca catcgaattg ccgggaaatt ggactttgag   1680

atcattttag ctccccaagg cgatccacac gtactctacc acaaaacttt ggttgttttt   1740

gctatcatct caaggccact gcagcatgcg cattgcgcac gtacgagatg ctactctttc   1800

caaggaaccg atgtctctct ctctctctcc agcctccatt gcttataaat atgttcctcc   1860

ttcctatact ggtaatggca gcaaagcaaa gaaacaaaga agaagaagaa a            1911
```

<210> SEQ ID NO 3
<211> LENGTH: 1034
<212> TYPE: DNA
<213> ORGANISM: Oryza sativa L. Oc cell

<400> SEQUENCE: 3

```
agcttgtgca tggcctaaac acacactttg acacttgact ttgtgttgga atccattgat     60

tagccgctca atgcagcatc cccaatgcag aggtctcccc tctactccta gctctttgca    120

aaacccaatg tccaccattg acttcaattt ctcagtcttc cttgctcatg tctcccttgc    180

ccttctctca acttgggtca acttcattaa atttctccct tggtatgtgc aaaggctttg    240

aaggtgtagg cctggtgcaa acattgcaaa gtcaaaatgt acggtacgat gcatcgattt    300

actgacatgg taatcttccc gattcccgtg taaataaact actatttcat tcgtttcatt    360

tataagatgt tttaattttg ttatgggcca aaacttgctt aactttgaca tagtttattg    420

aaaaaaaata ggttagaaaa cttaaattca ggaaaaaaag ataggtgaga tatcctagta    480

taaccatctt ggtttggtta agacatgcct tagaatagac gagtcggtcg aaacggtcag    540

aatcggtagc gtccctttag aaacgacgct caatcgacct gtaattgacc gtatttatca    600

tttacaacat taatacaatg caaaaagaaa ttagaaattt ttttataaat agtcaaaaat    660

ggtacgccag tctatcggga atttatgtga ccgttttcac ccctattcga gtgcatgggc    720

acttgagttg taaaattgac ttgatcgaga taccaacgta tatacaattt acacatcgaa    780

ttgccgggaa attggacttt gagatcattt tagctcccca aggcgatcca cacgtactct    840

accacaaaac tttggttgtt tttgctatca tctcaaggcc actgcagcat gcgcattgcg    900

cacgtacgag atgctactct ttccaaggaa ccgatgtctc tctctctctc tccagcctcc    960

attgcttata aatatgttcc tccttcctat actggtaatg gcagcaaagc aaagaaacaa   1020
```

-continued

```
agaagaagaa gaaa                                                         1034


<210> SEQ ID NO 4
<211> LENGTH: 563
<212> TYPE: DNA
<213> ORGANISM: Oryza sativa L. Oc cell

<400> SEQUENCE: 4

atcctagtat aaccatcttg gtttggttaa gacatgcctt agaatagacg agtcggtcga     60

aacggtcaga atcggtagcg tccctttaga aacgacgctc aatcgacctg taattgaccg    120

tatttatcat ttacaacatt aatacaatgc aaaaagaaat tagaaatttt tttataaata    180

gtcaaaaatg gtacgccagt ctatcgggaa tttatgtgac cgttttcacc cctattcgag    240

tgcatgggca cttgagttgt aaaattgact tgatcgagat accaacgtat atacaattta    300

cacatcgaat tgccgggaaa ttggactttg agatcatttt agctccccaa ggcgatccac    360

acgtactcta ccacaaaact ttggttgttt ttgctatcat ctcaaggcca ctgcagcatg    420

cgcattgcgc acgtacgaga tgctactctt tccaaggaac cgatgtctct ctctctctct    480

ccagcctcca ttgcttataa atatcttcct ccttcctata ctggtaatgg cagcaaagca    540

aagaaacaaa gaagaagaag aaa                                            563


<210> SEQ ID NO 5
<211> LENGTH: 5392
<212> TYPE: DNA
<213> ORGANISM: Oryza sativa L. Oc cell

<400> SEQUENCE: 5

gaattcctgg tttagttttc tattagttgg gcacaagatc ataactgcag tattgtattt     60

aagattcaac acaggttcaa tttgtcacac cctgtaattt ggcatctaca atctgaaaat    120

gaatggctaa tcaaaaggct ctgagcacac aaatggctaa tttcttccat ctagttgaga    180

aacctttcaa ttatacaaat ggaaaagata tggatgtgat ttgtgggctg aaaacccttt    240

gataatcaac aattgttagt gccttcaact ttcaatgcac ccatgttttc ttgttacgtt    300

tgcaagatca aaacaatgtt ggaaacgtca tctcgccagg taaagcaatg aatgacgaca    360

attaagaaga tttttgctcc tgaagactac taatgatgga tattaagggt ataataacct    420

atccaggatt gtgatgttca atccccttgt agcatacctg ataagtgtgg tgagttaaaa    480

gcagtcccat ttacaaaaag aaaaaggaag gcccatatct agcaaaaaaa atagactgca    540

tacgtatagt tgtttgtgaa aaagttcaag atgcatacaa gccgcagttt tcttcagata    600

gtgtggcatc ttcttacttc aaggaaaaaa acattatgct agtttggaaa taacttcaaa    660

tttgtccctg tgatggaaat taaaccattg gtaagtagtc tagcaatatc aaacttaagg    720

tgtgtgttgc atatgaatta ggaaaaacca tgtcaaacca actgaaacca aggaaaatcc    780

accatactaa catacttaaa taccttgagg tgagaaacat ataaagcata cagagaacat    840

gattagtaag aatgacgaag ataaaataca ctaaggtaat tagggaaaac agcaaagttc    900

atttggacat ttgatatcat ggaaagctat agaaaaatgt gtaccttaca gaccgaaatg    960

gaaagagtcc acgataaaaa gtcatttttg caccattttc cattgtaata cttatcgaga   1020

caaatttatg cgcgcacctt ttttccccca tccatccaaa taaattttta ttggtaaaac   1080

ttgttgcttt atgacagcag gaagtatctt ttacaatcta atgtacccat cagtacaata   1140

ttctagtagt atatctacaa caaaaataaa gatcaagggc atgcttggca catagaattt   1200
```

-continued

```
tgtatggaat tagttcaagt catttgttaa gcacataaat ttggcaaaac tctcatcttc   1260
caaattaacc ttgcaaaatt taaccaagaa aaactatata ctatcatccc gttccatgtc   1320
cttcctagta gcaaactttt tatgcaacca tttttttttc tcgacagggc attattcgtg   1380
gttactgtgt gcattaatag cattaataac agctagcatg tgagcctgtt attaggggta   1440
ggcagaaaga tctgaaccga aaagaccgac accgagtaaa tttggtcatc aattcggtcc   1500
tatatagtga aagaccgaac tttattcggt caattcggtt agtctcctcg gttaaccgaa   1560
tagacgaaag accaaattaa caaaaaaaaa atctaaatgc aacctacaat ccaccaagtt   1620
caatataatt aaactctaat tttcacagcc ctacttcttc taggcatgca acgtaataag   1680
agtctttagt catacgtgct tatggatttg ttttgtgatt tttgtgttaa aaatttccat   1740
tatttctttg catatatgaa aatgttgctg aatttcggtc agaccgagac cgagaccgaa   1800
tttgtcggtc atgatatttt ttgcgttgaa atttggtctt tacttttcga agatcgagac   1860
cgaatatttc ggtcagaccg aatgcccacc cctacttgtt ctctctatac ccatatgtca   1920
ataataatta ttattatact cactccgttc taaactatga ggcacttcct ttttaatgaa   1980
aaatcaaact cgataacttt taattaaaaa taatactaat atatactaaa tattatgcat   2040
gttatatcac tatatttata ttttaaagta ctttcatgta atgctaattt catattcgtt   2100
aaaatataga tattataatt caagatggag gagtacaacc aaacagtaga ggatccactt   2160
cctctttatt tatgccaagt tattttagaa ccatgctcca cacaagacac gcacacatcg   2220
cattgacatg tgttaatttt gtttcgtgtg gaaaggcatg gaggccggtt ccccacaatg   2280
tccaatcgct gccaactctg cgagtagaga agggggagga atggaagctt gtgcatggcc   2340
taaacacaca ctttgacact tgactttgtg ttggaatcca ttgattagcc gctcaatgca   2400
gcatccccaa tgcagaggtc tcccctctac tcctagctct ttgcaaaacc caatgtccac   2460
cattgacttc aatttctcag tcttccttgc tcatgtctcc cttgcccttc tctcaacttg   2520
ggtcaacttc attaaatttc tcccttggta tgtgcaaagg ctttgaaggt gtaggcctgg   2580
tgcaaacatt gcaaagtcaa aatgtacggt acgatgcatc gatttactga catggtaatc   2640
ttcccgattc ccgtgtaaat aaactactat ttcattcgtt tcatttataa gatgttttaa   2700
ttttgttatg ggccaaaact tgcttaactt tgacatagtt tattgaaaaa aaataggtta   2760
gaaaacttaa attcaggaaa aaaagatagg tgagatatcc tagtataacc atcttggttt   2820
ggttaagaca tgccttagaa tagacgagtc ggtcgaaacg gtcagaatcg gtagcgtccc   2880
tttagaaacg acgctcaatc gacctgtaat tgaccgtatt tatcatttac aacattaata   2940
caatgcaaaa agaaattaga aatttttta taaatagtca aaaatggtac gccagtctat   3000
cgggaattta tgtgaccgtt ttcaccccta ttcgagtgca tgggcacttg agttgtaaaa   3060
ttgacttgat cgagatacca acgtatatac aatttacaca tcgaattgcc gggaaattgg   3120
actttgagat cattttagct ccccaaggcg atccacacgt actctaccac aaaactttgg   3180
ttgtttttgc tatcatctca aggccactgc agcatgcgca ttgcgcacgt acgagatgct   3240
actctttcca aggaaccgat gtctctctct ctctctccag cctccattgc ttataaatat   3300
gttcctcctt cctatactgg taatggcagc aaagcaaaga aacaaagaag aagaagaaag   3360
aagaagcagc agcaaaaaag ttgatcagtt aattagcaag tgtgttcttc tttcttttgg   3420
tgagagagag agagagagag agagagagag agatctcaga atggtgaatc caggaagaac   3480
agctagggca ctctgcctcc tatgccttgc tctcctcctg ctaggtcaag atacccattc   3540
caggaagctc ctgttgcagg agaagcacag ccatggcgtc ggcaacggca caaccaccac   3600
```

-continued

```
ccaggtcagc agaattagtt cagtatcgtt tcttcagctt attaaccgtg gccaaatttg   3660

aattctataa cttaatttta gagttgatgt ggatgtgtta ttaatcatag attatttctc   3720

aacattgggt tttatgccgc taataacaca tatgtaaaac ctttacaaac aaattatttt   3780

tcggtcgcta ataagcgtta cggcttataa ttttcctagt gaacagtgca tgcattttgc   3840

aaacttcttg ttggctctgg ttgcaacttg caagcacgca tatgcattga gagaagagtt   3900

catacacaca ctgtattata tatatgtaca tttggggtat aagatactaa aatgaaacag   3960

gagcatcgtg ttctgaaatg gcgtggcgtt cttgtttatt ttcagcttgt gtaattgctg   4020

gagggcaata gcatgggaaa acactctaat ctgaatctgt gacacctgga acagtagcac   4080

cattcttgat ggcataatca tgtcttaacc acatgtctat cgttggaatc ctggtacaat   4140

gctccgagct gcatcgatcc atccatgcat gttacctcca tgtgttcgaa gatgctatat   4200

atttgcatac gacaggcaca gcttcatgaa tgtacttcgg cactgtctta ccaaactccc   4260

ctccgtttca tattataagt catttgattt ttttttccta gtcaagtatg accaagctta   4320

tagaaaaaat tagaaacatc taaaataaca aactagtttc agaaaatcta acattgaata   4380

tattttgata atatatttgt tttgggttga aaatactagt atatttttca ataaacttgg   4440

tccaacttaa ctagaaaaaa aatcaaacga cttataatat gaaacggagg gagaactttc   4500

gttttgattt tccaaagaac gacattatct taattttaag acatcgttat tgtttttaaa   4560

ataataatag gatcactagt ttctattaca atatatttgt aaaacacaat aatatgacaa   4620

tattatagag gtagtactac tttttgatat ttccatacac ccaatctata aattgatcaa   4680

agtttctgct tccactctgt ttcgttcgtt cttgaaagtt ttcttctaac agtatgatga   4740

tcttgatcaa tcaggaacca agcagagaga atggaggaag tacaggttcc aataacaatg   4800

ggcagctgca gtttgattca gccaaatggg aagaattcca cacggattat atctacaccc   4860

aagatgtcaa aaacccataa tggctgttca tttatgattt gaactagtac tagtagctta   4920

taccttctgc gcgtcttttg ttcgtttgga gaggggattt tcttgggatt tagcatatga   4980

actaattaaa ttaaatccca ggcaaatccc actcagccca ttttgtgcag aagttgtcag   5040

tgtgcactgt ataattattt agtcatacac aactactcct ggtaactact cctatcttcg   5100

atgaattttc tggttttgcc agacgtgaca atagtccagt agcatgcagt accctctcag   5160

aatccctgta atttttagca aaaaaaaaag gaagaaaaga aaagaagctt ccctactttc   5220

tccgtttcac aatgtaagtc attctagcat tttctacatt catattgatg ttaatgaatc   5280

tggatagata tatactccct ccgtcgaaaa aaaaaaaggc aaactgtggg ttccgtgcta   5340

acgtttgact gtccgcttat atgaaatttt tttataatta ggattttcat tg           5392
```

<210> SEQ ID NO 6
<211> LENGTH: 32
<212> TYPE: DNA
<213> ORGANISM: Artificial Sequence
<220> FEATURE:
<223> OTHER INFORMATION: Primer for primer extension analysis and S1 mapping

<400> SEQUENCE: 6

```
agcaggagga gagcaaggca taggaggcag ag                                   32
```

PROMOTER DERIVED FROM PHYTOSULFOKINE PRECURSOR GENE

BACKGROUND OF THE INVENTION

1. Field of the Invention

This invention relates to a promoter of phytosulfokine precursor derived from rice and a transgenic plant produced by incorporation of the promoter to activate expression of an exogenous structural gene.

2. Description of Related Art

In the field of plant genetic engineering, a promoter is ligated to upstream of an exogenous gene of target, which is a conventional technique for over-expression of the exogenous gene. In many cases, expression of the exogenous gene is not sufficient without existence of such promoter. Various promoters are utilized for this purpose and the method using cauliflower mozaic virus is the most conventional technique in this art. Here, a promoter means a regulatory region existing 5'-upstream of a structural gene. It is known that binding of RNA polymerase to a promoter serves as an initiation signal of transcription.

The method utilizing cauliflower mozaic virus (CAMV) 35S promoter is an excellent method for over-expression of an exogenous gene. However, in some cases, the extent of expression of the exogenous gene is not sufficient, depending on the exogenous gene to be incorporated and the species of the host plant which is the target of gene incorporation. Thus, there have been strong demands on a promoter with higher activity. It is the object of this invention to obtain a novel promoter exhibiting higher potency to activate a structural gene, compared with the conventional CAMV35S promoter.

The inventors noticed phytosulfokine (PSK), which is a peptide growth factor of a plant, and performed investigation on the growth factor. PSK is one of growth factors contained in so-called "conditioned medium:CM", a medium once used for cell culture. It is known that PSK is secreted into extra-cellular medium and functions in the manner like autocrine. At performance of plant cell culture, various known hormones or nutritional elements are added to the culture medium as a conventional technique. However, in some plant species, cell culture is itself difficult or rate of cell proliferation is extremely slow. Moreover, when the density of a plant cell is lower than necessary, proliferation of the plant cell becomes difficult. Even in such cases, PSK is effective to enhance proliferation of a plant cell. It is also known that, the structure of PSK-α and PSKβ are defined by the following sequences wherein tyrosine residues of the PSKs are sulfated by post-translational modification.

PSK-α: Tyr($SO_3$H)—Ile—Tyr($SO_3$H)—Thr—Gln

PSK-β: Tyr($SO_3$H)—Ile—Tyr($SO_3$H)—Thr

The PSK-α and PSK-β are extra-cellular secreted peptides bio-synthesized in the form of their precursor, sulfated and processed during their transition via trans-Golgi network. The cDNA sequence of *Oryza sativa* phytosulfokine (OsPSK) have been already determined, using the technique of cDNA cloning. Moreover, the cDNA thus obtained and the polypeptide encoded by the cDNA are described in Japanese Patent Publication No. 11-079612. Incorporation of said gene into a plant would enhance proliferation of a plant.

SUMMARY OF THE INVENTION

One aspect of this invention is a promoter consisting of a base sequence of following (a), (b) or (c):

(a) a base sequence represented by base numbers −3359 to −1 shown in SEQ:ID NO:1 in the sequence list, (b) a base sequence in which a part of said base sequence (a) is deleted or another base sequence is added to said base sequence (a) or a part of base sequence (a) is substituted with another base sequence, the base sequence (b) exhibiting activity to enhance expression of a structural gene existing downstream of the promoter, or (c) a base sequence that hybridizes with the base sequence (a) under stringent conditions.

Further aspect of this invention is a promoter consisting of a base sequence of following (d), (e) or (f):

(d) a base sequence represented by base numbers −1911 to −1 shown in SEQ:ID NO:2 in the sequence list, (e) a base sequence in which a part of said base sequence (d) is deleted or another base sequence is added to said base sequence (d) or a part of base sequence (d) is substituted with another base sequence, the base sequence (e) exhibiting activity to enhance expression of a structural gene existing downstream of the promoter, or (f) a base sequence that hybridizes with the base sequence (d) under stringent conditions.

Further aspect of this invention is a promoter consisting of a base sequence of following (g), (h) or (i):

(g) a base sequence represented by base numbers −1034 to −1 shown in SEQ:ID NO:3 in the sequence list, (h) a base sequence in which a part of said base sequence (g) is deleted or another base sequence is added to said base sequence (g) or a part of base sequence (g) is substituted with another base sequence, the base sequence (h) exhibiting activity to enhance expression of a structural gene existing downstream of the promoter, or (i) a base sequence that hybridizes with the base sequence (g) under stringent conditions.

Further aspect of this invention is a promoter consisting of a base sequence of following (j), (k) or (l):

(j) a base sequence represented by base numbers −563 to −1 shown in SEQ:ID NO:4 in the sequence list, (k) a base sequence in which a part of said base sequence (j) is deleted or another base sequence is added to said base sequence (j) or a part of base sequence (j) is substituted with another base sequence, the base sequence (k) exhibiting activity to enhance expression of a structural gene existing downstream of the promoter, or (l) a base sequence that hybridizes with the base sequence (e) under stringent conditions.

Further aspect of this invention is a gene encoding phytosulfokine precursor consisting of a base sequence represented by base numbers −3359 to 2033 shown in SEQ:ID NO:5 in the sequence list.

Further aspect of this invention is a plasmid in which above described promoter was incorporated. Moreover, a transgenic plant cell in which above described promoter was incorporated to activate expression of a structural gene existing downstream of the promoter is also within the range of this invention. Moreover, a transgenic plant body in which above described promoter was incorporated to activate expression of a structural gene existing downstream of the promoter is also within the range of this invention.

Further aspect of this invention is a method to activate expression of an endogenous structural gene or an exogenous structural gene in a plant by incorporation of above described promoter into upstream of the structural gene.

BRIEF DESCRIPTION OF THE DRAWINGS

The above and other objects and features of the present invention will be further explained in detail hereinafter from consideration of the following description taken in connection with the accompanying drawings, in which:

FIG. 4 is a figure showing base sequence of OsPSK gene and its deduced amino acid sequence;

DETAILED DESCRIPTION OF THE INVENTION

Figure 1:
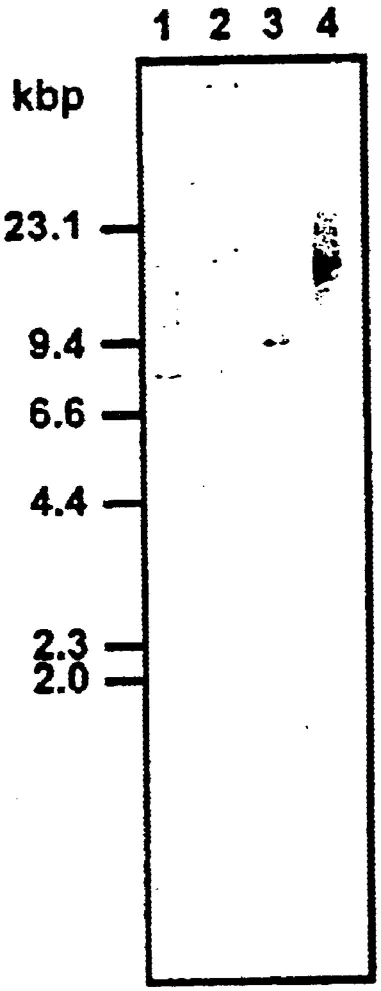
FIG. 1 is a photograph of blotting analysis performed on genomic DNA of rice Oc cell using cDNA of OsPSK as a probe.

The inventor noticed the above-described knowledge and investigated to obtain a promoter that regulates expression of the OsPSK gene. Meanwhile, the base sequence described in Japanese Patent Publication No. 11-079612 is a cDNA sequence obtained by transcriptase reaction using mRNA as a template. Therefore, the sequence does not include non-translated region of the gene and the region corresponding to intron. In general, a regulatory region like a promoter is not translated. Therefore, it is requisite to prepare genomic DNA library, originated from total DNA of a cell, to obtain genomic DNA of OsPSK including regulatory region. Then, the inventors have prepared genomic library of OsPSK and performed cloning by plaque hybridization using the cDNA as a probe. As the result, full-length genomic sequence of PSK precursor gene was obtained and non-translated region and intron were included in the sequence. In the genomic sequence, it was revealed that a promoter exists upstream of its open reading frame region and the promoter includes various consensus sequences. Beta-glucuronidase (GUS) was incorporated downstream of the promoter and the potency of the promoter to activate expression of GUS gene was investigated. As the result, the potency of this promoter to activate GUS gene was higher than that of CAMV35S promoter. Therefore, it was shown that the promoter might be a useful tool that enables constitutive activation of expression of an exogenous gene.

This invention is a gene encoding phytosulfokine precursor polypeptide, consisting of a base sequence defined by base numbers from −3359 to 2033 in SEQ.ID No.5 in the sequence list. This is a genomic DNA sequence encoding PSK precursor, obtained by screening of the genomic library by plaque hybridization using 32P-labeled cDNA as a probe. The genomic DNA sequence and the cDNA sequence of the PSK precursor, which have already obtained, were compared and it was revealed that the genomic DNA sequence consisted of two exons and one large intron. The sequence encoding PSK, consisting of 5 amino acids, existed in the second exon. In SEQ.ID No.5 in the sequence list, base numbers from 1 to 1858 corresponds to the transcriptional region. The region of base numbers from 246 to 1395 corresponds to the intron and the region of base numbers from 1396 to 1858 corresponds to the second exon including PSK coding region. Moreover, the region of base numbers from 1396 to 1521 corresponds to the 3' downstream purlieu sequence. A putative TATA box was found at the position of −68 and consensus sequences of potential regulatory elements were found further upstream of the sequence. Those are, one CAAT-box, three CCAAT-boxes, three SSREs (shear-stress-responsive element), one enhancer core-like sequence and three E-boxes. Those are consensus sequences commonly recognized among many organisms and involved in regulation of transcription. It is known that a certain protein binds to each of these consensus sequences. When such binding occurs, the frequency of transcription is regulated by interaction between the protein and the DNA.

As described in the following embodiment, a plasmid containing fusion gene comprising 5'-region of OsPSK gene and β-glucuronidase (GUS) gene was prepared. The effect of 5'-region of OsPSK gene on GUS activity was investigated. As the result, the region containing 5'-regulatory elements enhanced activity of GUS gene and the potency was higher than that of CAMV35S promoter. Such promoter sequence derived from 5' region of OsPSK gene is defined by base numbers from −3359 to −1 in SEQ.ID No.1 in the sequence list. The promoter is regulatory region of OsPSK gene and the region corresponds to the sequence utilized to incorporate into plasmid pIG121-6 in the following example (refer to FIG. 5). In the OsPSK gene, the sequence is the longest sequence of the promoter that exhibits activity as a promoter and if a sequence longer than it was adopted, the activity as a promoter would decrease significantly.

The 5' region of OsPSK gene maintains activity as a promoter, even if a shorter sequence of SEQ.ID No.1 is adopted. Promoter consisting of the sequence defined by base numbers from −1911 to −1 in SEQ.ID No.2 in the sequence list is one of such promoter. The region corresponds to the sequence was utilized to incorporate into plasmid pIG121-4 in the following example (refer to FIG. 5). In the OsPSK gene, this sequence corresponds to the region that exhibits maximum activity as a promoter.

The promoter consisting of the sequence defined by base numbers from −1034 to −1 in SEQ.ID No.3 in the sequence list, is also one of such region of the promoter that maintains activity as a promoter. The region derived from the OsPSK gene corresponds to the sequence utilized to incorporate into plasmid pIG121-3 in the following example (refer to FIG. 5).

Furthermore, the promoter consisting of the sequence defined by base numbers from −563 to −1 in SEQ.ID No.4 in the sequence list, is also one of such region of the promoter that maintains activity as a promoter. The region derived from the OsPSK gene corresponds to the sequence utilized to incorporate into plasmid pIG121-2 in the following example (refer to FIG. 5). This sequence corresponds to the minimum region of OsPSK gene that exhibits activity as a promoter. If a sequence shorter than it was adopted, the activity as a promoter would decrease significantly.

According to technique of gene recombination, artificial modification can be achieved at a specific site of basic DNA, without alteration or with improvement of basic characteristic of said DNA. Concerning a gene having native sequence provided according to this invention or modified sequence different from said native sequence, it is also possible to perform artificial modification such as insertion, deletion or substitution to obtain gene of equivalent or improved characteristic compared with said native gene. Moreover, a gene with such mutation is also included in the range of this invention. A promoter consisting of a base sequence in which a part of said promoter consists of base sequence shown in SEQ ID NO: 1 is deleted, substituted or added with one or more bases means a promoter in which a part of said promoter consists of base sequence shown in SEQ ID NO: 1 is deleted, substituted or added with one or more bases while maintaining activity as a promoter to enhance expression of a structural gene existing in the downstream of the promoter. Such promoter exhibits homology 70% or more, preferably 80% or more and still preferably 90% or more with the amino acid sequence shown in SEQ ID NO: 1 in the sequence list. Moreover, concerning such promoter, the number of bases deleted, substituted or added compared with the base sequence shown in SEQ ID NO: 1 is 20 or less, preferably ten or less, and more preferably five or less. In addition, such promoter hybridizes with the base sequence shown in the SEQ ID NO: 1 in the sequence list thereof under stringent condition. Then, a promoter consisting of a base sequence in which a part of said promoter consists of base sequence shown in SEQ ID NO: 2, SEQ ID NO: 3 or SEQ ID NO:4 is deleted, substituted or added with one or more bases means the same variations of the base sequences.

A plasmid, in which the promoter derived from OsPSK gene was incorporated, is also within the scope of this invention. In the following example, pIG121 plasmid containing CaMV35S promoter and GUS reporter gene was adopted, but the scope of this invention is not to be limited to it. For example, other plasmids conventionally utilized in the art, such as pIG122, pBI101, pBI121, pBI221, pAct-nos/Hmz, pMAT037, pTA7001 and pTA7002, can be also adopted.

A transformed plant produced by incorporation of the promoter of this invention to enhance expression of an exogenous gene is also within the scope of this invention. The example of plants, preferred as a target of incorporation of the promoter of this invention to activate expression of an exogenous gene, may include monocotyledonous plants, such as rice, lily, maize, asparagus and wheat, as well as dicotyledonous plants, such as tobacco, *Arabidopsis thaliana*, carrot, soybean, tomato and potato. In principal, any plant can be adopted to incorporate the promoter of this invention thereby activate expression of an exogenous gene. In the following example, *Agrobacterium tumefaciens* LBA4404 strain was adopted, but not the scope of this invention is not to be limited to the strain. According to the species of the plant, which is the target of incorporation, an Agrobacterium strain conventionally utilized in this art can be properly selected and adopted.

In principal, any useful structural gene can be adopted as an exogenous gene of target to be incorporated downstream of the promoter to activate expression of the exogenous gene. In the following embodiment, GUS gene was incorporated but the scope of this invention is not to be limited to it. The example of exogenous genes to be incorporated may include a gene encoding a factor that enhances growth of a plant, a gene involved in resistance against various environmental stresses, a gene involved in resistance against disease injury of a plant, a herbicide resistance gene and a gene encoding an enzyme involved in synthesis of a useful secondary metabolite.

Moreover, a plant body obtained from a transgenic plant cell thus produced to activate expression of an exogenous gene and a method to produce a transformed plant cell are also within the scope of this invention. In the following embodiment, this invention is elucidated in detail using rice culture cell as an example, above description and following embodiment is not to be considered to limit the scope of this invention.

Embodiment

Plant Cell Culture

Rice Oc culture cells (Baba et al., 1986) were subcultured at 25±2° C. in the dark at 120 rpm in fresh Murashige and Skoog medium (MS; Murashige and Skoog, 1962) supplemented with 1 mg/l of 2,4-dichlorophenoxyacetic acid (2,4-D) at regular intervals of 2 weeks.

(Genomic DNA Extraction and Southern Blot Analysis)

Genomic DNA was extracted from rice Oc culture cells cultured for 14 days using the CTAB method (Murry and Thompson, 1980), digested with restriction endonucleases, separated by electrophoresis on 0.8% (w/v) agarose gels, and blotted onto Biodyne nylon membranes (Pall, Port Washington, N.Y., USA) in alkaline transfer buffer (0.4 N NaOH/0.6 N NaCl). Southern hybridization was performed in a solution of 5×SSC, 0.5% SDS, 5×Denhardt's solution and 500 μg/ml Salmon sperm DNA at 50° C. or 65° C. using the OsPSK cDNA $^{32}$P-labeled with a Random Primed DNA Labeling Kit (Takara, Tokyo, Japan). After hybridization, washing was performed with 2×SSC at 25° C. 15 min for 3 times and then 2×SSC containing 0.1% SDS at 50° C. or 65° C. 15 min for 3 times.

Construction and Screening of a Genomic Library

Genomic DNA (50 μg) was partially restricted with Sau3A I to generate BamHI-compatible fragments ranging in size from 9 to 23 kb. The genomic fragments (0.3 μg) were inserted into the BamHI site of EMBL3 vectors that had been digested with BamHI and EcoRI (Stratagene, La Jolla, Calif., USA) and packaged with Gigapack III Gold Packaging Extract (Stratagene) to construct a genomic library. This was screened by plaque hybridization with the $^{32}$P-labeled OsPSK cDNA. Hybridization and washing were executed under high stringency conditions at 65° C. as described above.

Subcloning and DNA Sequencing

Restriction mapping of positive genomic clones was carried out by single and double restriction enzyme digestion. A series of fragments spanning the OsPSK gene were excised from positive phages, gel-purified, and subcloned into the corresponding sites of pBluescript II-KS (pBS) plasmids. Deletion clones were generated for DNA sequencing with a Kilo Sequencing Kit (Takara) according to the protocol recommended by the manufacturer. The plasmids containing the deleted fragments were introduced into *Escherichia coli* strain JM109 and sequenced completely on both strands. Double-stranded DNA sequencing reactions were run using a BigDye Terminator Cycle Sequencing Kit (Applied Biosystems, Foster, Calif., USA), and analysis of the DNA sequence data was performed using an ABI PRISM 310 Genetic Analyzer (Applied Biosystems) in accordance with the manufacturer's protocols.

Determination of Transcriptional Start Site

The transcriptional start site was established by both primer extension and S1 nuclease analysis. Total RNA extracted from 2-week-old Oc culture cells after transplanting and a 32 nucleotide long primer with the sequence 5'-AGCAGGAGGAGAGCAAGGCATAGGAGGCAGAG-3' (SEQ ID NO: 6) which is complementary to a region 32 nucleotides downstream of the ATG start codon in the OsPSK cDNA were used for both analyses. The oligonucleotide primer was 5'-end-labeled with 10 U of T4 polynucleotide kinase (Takara) and 30 μCi of [γ-$^{32}$P]-ATP (3000 μCi/mmol). End-labeled primer was annealed with 10 μg of total RNA for 1 h at 60° C. The primer extension reaction was carried out according to the published procedure (Sambrook et al., 1989) at 37° C. for 1 h with 20 U of Moloney murine leukemia virus reverse transcriptase (Stratagene). For S1 mapping, a 3.6-kb EcoRI fragment from the OsPSK gene and the end-labeled primer were used to synthesize one strand DNA. A 315-b fragment was excised and purified from the synthesized DNA with PstI and used as the S1 probe, hybridized to 30 μg of total RNA at 60° C. and incubated with 300 units/ml S1 nuclease (Takara) for 30 min at 30° C. The reaction products in both experiments were run side by side on a 6% polyacrylamide gel containing 7 M urea.

Construction of Chimeric Genes

The plasmid pIG121 contains the cauliflower mosaic virus (CaMV) 35S promoter, a modified intron of the castor bean catalase gene, and the GUS reporter gene (Akama et al., 1992). This CaMV 35S-Intron-GUS reporter gene is expressed in plants but not in cells of *Agrobacterium tumefaciens* (*A. tumefaciens*) (Ohta et al., 1990). The pIG121 harbors a kanamycin resistance gene which can be used to select transformants. The plasmid pIG121 was digested by HindIII-XbaI to remove the CaMV 35S promoter and various fragments from the 5' region of the OsPSK gene were inserted into the HindIII-XbaI sites of the binary vector to construct chimeric genes as follows. A 241-bp PstI-BglII fragment from the 5' region of the OsPSK gene was subcloned into pBS at the PstI-BamHI sites to generate pBS-1. The fragment was excised by HindIII-XbaI from pBS-1 and cloned between the same sites of the promoter-less pIG121 to construct pIG121-1. Introduction of a 662-bp HindIII-XbaI fragment from pBS-2 containing the EcoRV-BglII fragment into the same sites of the promoter-less pIG121 produced pIG121-2. The 1.1-kb HindIII-BglII fragment of the 5' region of the OsPSK gene was subcloned into the HindIII-BamHI sites of pBS to produce pBS-3. The plasmid pIG121-3 was generated by introduction of the 1.1-kb fragment from pBS-3 into the HindIII-XbaI sites of the promoter-less pIG121. The 2-kb BglII-BglII fragment of the 5' region of the OsPSK gene was subcloned into the BamHI site of pBS to produce pBS-4. A 877-bp HindIII-HindIII fragment was excised from pBS-4 and inserted into the same site of pIG121-3 in both possible orientations to produce pIG121-4 and pIG121-5. The 3.7-kb EcoRI-EcoRI fragment of OsPSK was isolated and cloned into the same site of pBS to produce pBS-5, which was then cleavaged by HindIII and the 2.3-kb fragment inserted into the same sites of pIG121-3 in both possible orientations to construct pIG121-6 and pIG121-7.

Here, the sequence incorporated into pIG121-1 corresponds to the region represented by base numbers from −148 to −1 in SEQ ID NO: 1 in the sequence list. The sequence incorporated into pIG121-2 corresponds to the region represented by base numbers from −563 to −1. The sequence incorporated into pIG121-3 corresponds to the region represented by base numbers from −1034 to −1. The sequence incorporated into pIG121-4 corresponds to the region represented by base numbers from −1911 to −1. The sequence incorporated into pIG121-5 is the same region incorporated into pIG121-4, but the region corresponding to base numbers from −1911 to −1034 is incorporated in the reverse orientation. The sequence incorporated into pIG121-6 corresponds to the region represented by base numbers from −3359 to −1. The sequence incorporated into pIG121-7 is the same region incorporated into pIG121-6, but the region corresponding to base numbers from −3359 to −1034 is incorporated in the reverse orientation.

Agrobacterium-Mediated Transformation of Rice Oc Cells

The constructs were transformed into *A. tumefaciens* strain LBA4404 by triparental matting. For Agrobacterium-mediated transformation, *A. tumefaciens* cells were grown for 3 days on AB agar medium containing 50 mg/liter kanamycin at 30° C. in the darkness. The bacteria were collected with a small spoon, and suspended in AAM medium (Yang et al., 2000a) at a density of $OD_{600}$=0.2. Oc cells (0.5 ml packed cell volume) that were pre-cultured for 3 days at 25° C. in the dark on fresh MS medium supplemented with 1.0 mg/l of 2,4-D prior to infection were immersed in 4 ml of the bacterial suspension in 90 mm×20 mm Petri plates (Terumo, Tokyo, Japan). The plates were sealed with parafilm and co-cultivation was carried out in the dark at 28° C. for 3 days. After 3 days of inoculation, cultures were collected into Falcon 2097 tubes. Oc cells were collected by centrifugation at 1,000 rpm (MX-160 centrifuge, TMA-27 angle rotor; Tomy) for 1 min, resuspended in MS medium, mixed well by gentle vortexing, and then centrifuged at 1,000 rpm for 1 min. After centrifugation, the supernatant was discarded. This rinsing process was repeated for 3 to 5 times to exclude *A. tumefaciens* cells. The rinsed Oc cells were cultured on fresh MS medium supplemented with 1.0 mg/l of 2,4-D, 50 mg/l kanamycin, and 250 mg/l cefotaxime to select transformed cells.

Quantitative Analysis of GUS Activity

More than 5 independent transformed cell lines for each construct were cultured for 7 days on selection medium for measurement of GUS activity. Total soluble protein was isolated from the transformed Oc cells in a GUS extraction buffer (Jefferson et al., 1987) and activity was quantitatively assayed by the fluorometric reaction procedure of Jefferson et al. (1987) using 4-methylumbelliferyl-β-D-glucuronide (Sigma, St. Louis, Mo., USA). The amount of protein was determined with a Bio-Rad Laboratories kit by the method of Bradford (1976).

RNA Isolation and Northern Blot Analysis

Oc cells transformed with the plasmid pIG121-4 were cultured for 0, 12, 24, 48, and 72 h, respectively, in MS media supplemented with different combinations of phytohormones: 2 mg/l of 2,4-D only, 2 mg/l of 6-BA only, or 1 mg/l each of 2,4-D and 6-BA. Total RNA (20 μg per lane) isolated from various samples by a published method (Chomczynski, 1993) was denatured and fractionated by electrophoresis on 1.2% (w/v) agarose gels containing 2.2 M formaldehyde. The RNAs were subsequently transferred to Biodyne nylon membranes (Pall) in 20×SSC. The filters were hybridized to a random-primed probe of the gusA gene as described above.

Copy Number of OsPSK Gene

The inventors previously characterized OsPSK cDNA in rice encoding the precursor of PSK-α, a peptide growth factor identified from plants. Prior to the isolation of genomic clones corresponding to OsPSK cDNA, the copy number of this gene in the rice genome was investigated by genetic Southern blotting. DNA blot analysis under low stringency conditions using the full-length OsPSK cDNA as a probe revealed only one band in DNA digested with three different restriction enzymes, except EcoRI that generated two strong and one weak hybridizing bands (Yang et al., 1999). When the Southern blot was hybridized to the probe under high stringency conditions, only the strong bands were detected in EcoRI-digested DNA (data not shown). These two hybridizing bands were expected by the restriction site residing in the coding region of OsPSK cDNA. To verify this notion, the inventors reprobed the blot using a 300-bp fragment from the 5' terminus of OsPSK cDNA. As expected, only one band of 3.6 kb was hybridized under either low or highly stringent conditions. In FIG. 1, the genomic DNA isolated from rice Oc cells was digested with either BamH I (lane 1), EcoR I (lane 2), Xba I (lane 3) or Xho I (lane 4) and hybridized with the radio-labeled probe derived from 5' end of the OsPSK cDNA. The result indicated that OsPSK is a single-copy gene. Indeed, screening of a genomic library allowed the isolation of only one group of genomic clones.

Isolation of the OsPSK Gene

Figure 2A:
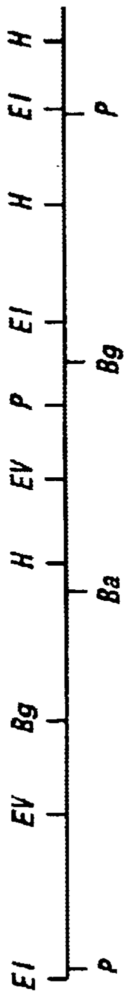
FIG. 2 is a schematic figure showing restriction map of OsPSK genomic gene and genomic structure of the OsPSK gene.
Figure 2B:
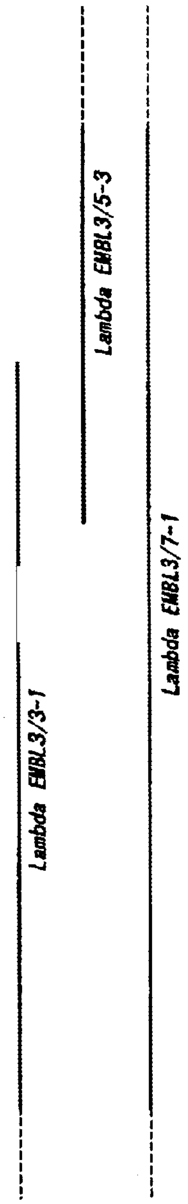
Figure 2C:
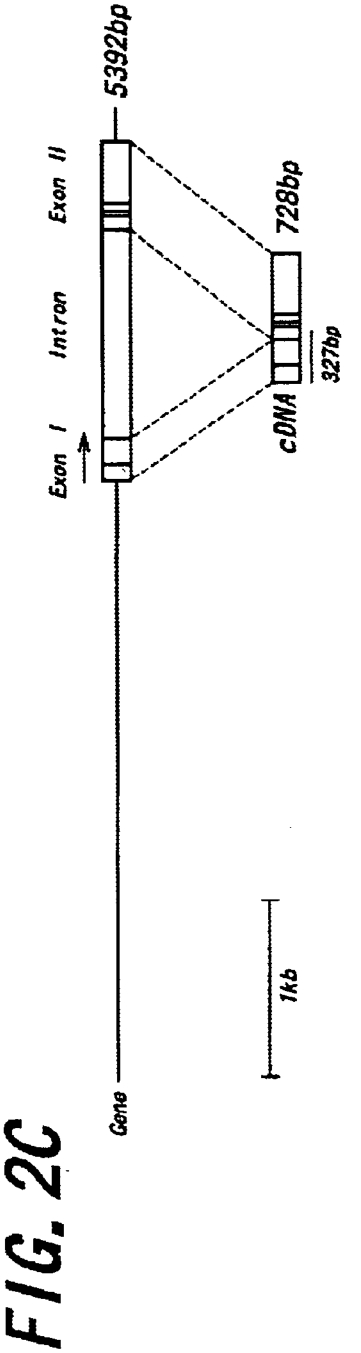

A genomic library was constructed with λEMBL3 phages and Sau3AI-digested DNA fragments prepared from rice Oc culture cells, and screened by plaque hybridization with the OsPSK cDNA as a probe. Three overlapping clones, namely, λEMBL3/3-1, λEMBL3/5-3, and λEMBL3/7-1, carrying fragments derived from the OsPSK gene were obtained (FIG. 2B). These clones, classified into 3 subgroups, overlapped and spanned a region of more than 45 kp of the rice genomic DNA. To begin analyses of the OsPSK genomic structure and regulatory regions, the inventors carried out restriction mapping of the three λEMBL3 phage clones (FIG. 2B) by single and double restriction enzyme digestion as well as Southern hybridization. The resulting restriction map of the genomic fragment flanking the OsPSK gene is shown in FIG. 2A. In FIG. 2, the restriction sites are abbreviated as follows : Ba;BamHI, Bg;BglII, El; EcoRI, EV; EcoRV, H;HindIII, P;PstI. The 22.8-kb λEMBL3/7-1 insert was found to contain the entire OsPSK gene including the 5' -upstream region, the full-length transcribed sequence corresponding to OsPSK cDNA, the non-coding intron, and the 3'-downstream region. In FIG. 2C, the transcription direction of the OsPSK gene is marked by a horizontal arrow and the intron is shown by an open box. Noncoding and coding portions of OsPSK exons are indicated by shaded and striped boxes, respectively. The sequence encoding PSK-α within the second exon is depicted by a white bar. The horizontal bar labeled “327-bp” represents the probe used for genomic DNA hybridization.

Determination of the Transcription Start Site of the OsPSK Gene

Figure 3:
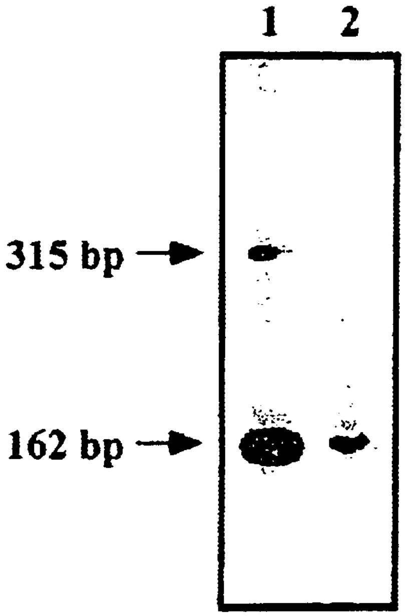
FIG. 3 is a photograph showing result of primer extension reaction and S1 mapping.

The transcription start site of the OsPSK gene was determined by primer extension analysis and S1 mapping (FIG. 3). In FIG. 3, the reaction products of the S1 nuclease (lane 1) and the primer extension (lane 2) experiments were subjected to electrophoresis on a polyacryamide gel. The sizes of the probe used for S1 mapping and the products in both experiments are indicated in kb on the left. The inventors used one 32-base-long oligodeoxyribonucleotide corresponding to the 5'-end region of the OsPSK cDNA, as a primer (FIG. 4) and primer extension reaction was carried out. Total RNA extracted from Oc culture cells were used as a template, and products were analyzed by autoradiography after electrophoresis in a polyacrylamide gel. One band about 162-bases in length was detected from the extension product (FIG. 3). Next, the inventors prepared a 315-bp probe using a 3.6-kb EcoRI fragment from the OsPSK gene and the $^{32}$P-labeled primer followed by PstI digestion. Then the inventors performed S1 nuclease analysis using the $^{32}$P-labeled 315-bp fragment as a probe. After hybridization with total RNA and digestion with S 1 nuclease, a product of 162-bases was again detected (FIG. 3). This size is identical to that from the 5'-terminal residue to the position complementary to the primer. Therefore, the first guanidine of the OsPSK cDNA, located 62 nucleotides downstream of the TATA box, was arbitrarily designated +1. Most likely it represents the 5' end of the OsPSK transcript (FIG. 4).

Genomic Organization of the OsPSK Gene

The nucleotide sequence of a 7.4-kb region harboring the entire OsPSK gene in the genomic clone λEMBL3/7-1 was completely determined on both strands and its structure analyzed. In FIG. 4, nucleic acid and deduced amino acid sequences of the OsPSK gene were shown. The transcription initiation site is designated +1 and a putative TATA-box is boxed. A CAAT-box, three E-boxes, three CCAAT-boxes, a enhancer core-like sequence, and three SSREs are indicated with underlining. The consensus binding site for the regulatory nuclear protein SEF3 is marked by a striped line up the sequence. The most likely sequence for a polyadenylation signal is labeled by double underlining. The sequence complementary to the primer used for primer extension and S1 nuclease analyses is indicated by a dashed line. The vertical arrows show the positions used in the subsequent construction of the various OsPSK-Intron-GUS fusion plasmids. The amino acid sequence is represented using the single-letter amino acid code. The amino acid sequence of PSK-α is indicated by the bold capital letters and the translation termination codon is marked with an asterisk. Sequence comparison of this fragment and the cDNA revealed that the OsPSK gene consisting of two exons (245 bp and 463 bp), which perfectly match the cDNA sequence, is interrupted by a large intron of 1150 bp with a well-conserved GT-AG intron border sequence. An in-frame TGA stop codon was found 337 bp upstream of the Met codon of the first exon,including the 5' noncoding region and a coding region for about half of the PP-PSK (preprophytosulfokine), i.e. 48 out of 89 amino acid residues of the precursor, including the initiation methionine. A 22 amino acid $NH_2$-terminal hydrophobic region that presumably acts a signal was found in the first exon. The second exon was determined to consist of the 3' non-coding region and a coding region for the remaining 41 amino acid residues of the PP-PSK, within which the 5-amino acid PSK-α sequence occurred only once, close to the COOH-terminus. A poly adenylation signal consisting of an AAATTAA sequence was identified at positions 1629 to 1635.

Characterization of the 5'-Upstream Region of the OsPSK Gene

The inventors searched the 5'-upstream region of the OsPSK gene for known motifs of other genes and found several potential regulatory elements (FIG. 4). The consensus sequence of a putative TATA box (5'-TATAA-3') was found at positions −63 to −68, referring to the transcription initiation site. Upstream to this sequence, there are one CAAT-box at −267 to −270 and three CCAAT-boxes at −906 to −910, −949 to −953, and −1074 to −1078, respectively. Interestingly, the sequence AACCCA (at −908) conforms to the A(A/C/G)CCCA consensus sequence, the binding site of a soybean enhancer for the regulatory nuclear protein SEF3 (Allen et al., 1989), and an 8-nucleotide enhancer core-like motif (Weither et al., 1983; Hata et al., 1986), located at position −1105 to −1112 with the sequence 5'-GTGGAAAG-3'. Additionally, three E-boxes (consensus sequence: 5'-CANNTG-3'; Pabo, 1992), three shear-stress-responsive elements (SSRE: 5'-GAGACC-3'; Resnick et al., 1993), and several repetitive sequences are present in this 5'-end region. These findings suggest that transcription may be influenced by a variety of genetic elements.

Expression of OsPSK::GUS Chimeric Genes in Transformed Cells

Figure 5:
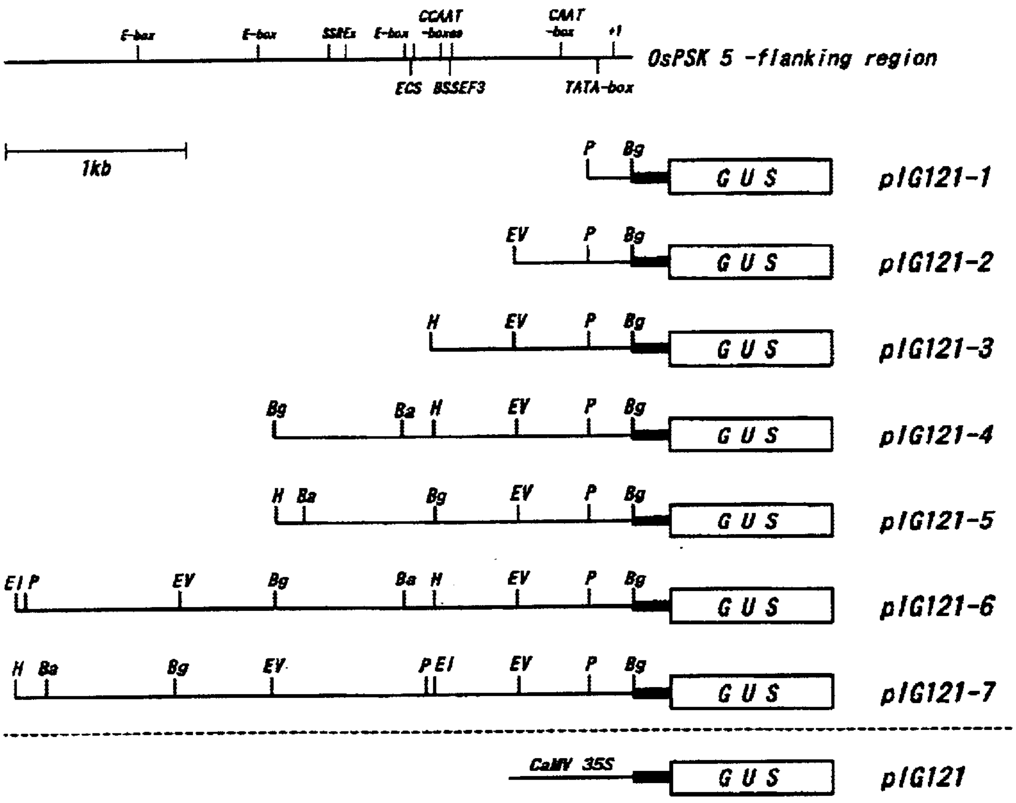
FIG. 5 is a figure showing structure of OsPSK-intron-GUS constructs.

To determine the OsPSK 5'-upstream sequence required for its expression, the CaMV 35S promoter in the plasmid pIG121 was replaced with various fragments from the 5' region of the OsPSK gene. In FIG. 5, the structure of OsPSK-Intron-GUS constructs were shown. A schematic diagram of the 5'-upstream region of OsPSK is shown at the top. The locations of the putative regulatory elements are indicated. Maps of constructs containing various portions of the 5'-upstream sequence (thick line) fused to the GUS gene (open box, not to scale) are shown next to their respective names. The indicated restriction enzyme sites are abbreviated as in FIG. 2. BSSEF3; the binding site of a soybean enhancer for the regulatory nuclear protein SEF3, ECS; enhancer core sequence, SSREs; shear-stress-responsive elements. Dashed lines indicate fragments in reverse orientation. As a positive control, the inventors used the original pIG121 containing the CaMV 35S promoter (Ohta et al., 1990). These constructs were introduced into Oc suspension culture cells via Agrobacterium infection, and transformed cells were selected on MS agar medium supplemented with 50 mg/l kanamycin (Yang et al., 1999). For each construct, the inventors assayed GUS activity (Jefferson et al., 1987) in more than 5 independent transformed cell lines. The results are presented in FIG. 6. The result of GUS activity is the mean of three independent experiments and indicated with the standard deviation.

The inventors constructed five OsPSK-Intron-GUS plasmids, pIG121-1, pIG121-2, pIG121-3, pIG121-4, pIG121-6, to determine the minimum length of the OsPSK 5'-upstream sequence required for maximal GUS activity. Transformed cells harboring these plasmids all displayed positive GUS activity and non-transformed cells as negative controls had no detectable GUS expression. The plasmid pIG121-1 harboring the shortest 5'-upstream region, which has no putative regulatory elements except TATA box, showed the lowest GUS activity. The highest was recorded for the plasmid pIG121-4, within which most of the 5'-putative regulatory elements including SSRE and enhancer core motif are located, indicating that the region 1.9 kb upstream of the OsPSK transcription initiation site has the minimal amount of OsPSK sequence necessary for maximal GUS expression in transformed Oc cells. The cells transformed with pIG121-6, with the longest OsPSK 5'-upstream region, displayed similar GUS activity to cells transformed with pIG121-4.

Figure 6:
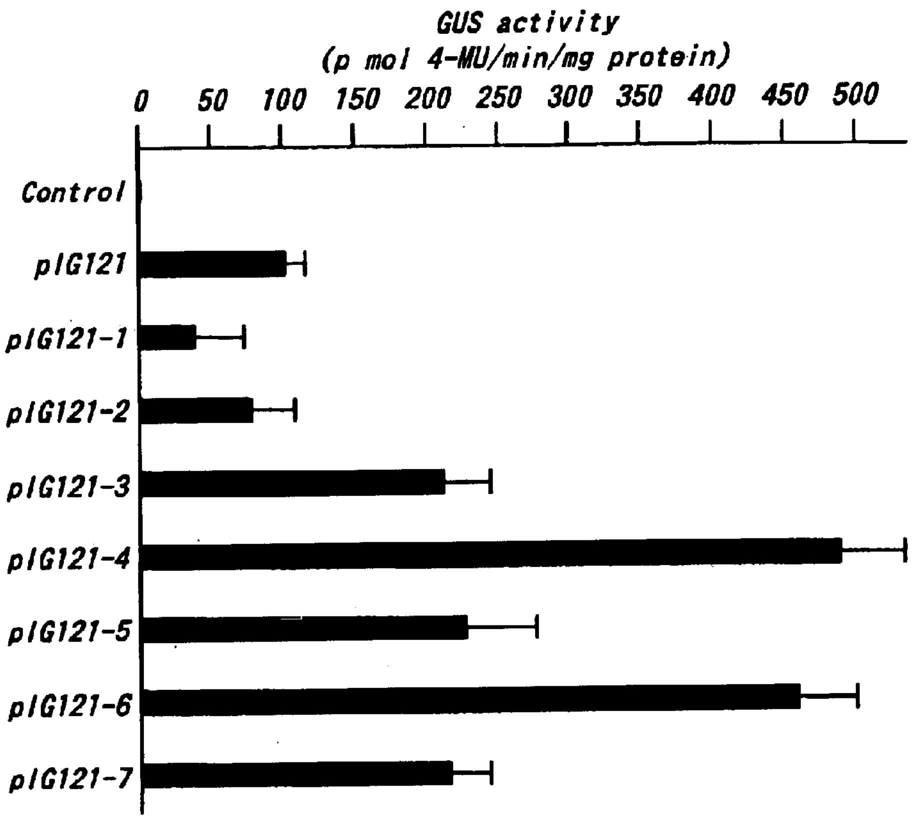
FIG. 6 is a graph showing GUS activity of transformed rice Oc cells transformed with OsPSK-intron-GUS constructs.

To test for any potential enhancer-like activity within the BglII-HindIII fragment of the OsPSK 5'-upstream region in pIG121-4 but not in pIG121-3, the inventors constructed the plasmid pIG121-5 containing the BglII-HindIII fragment in the opposite orientation to that in pIG121-4. The GUS activity in cells transformed with this construct markedly decreased the activity recorded in cells transformed with pIG121-4 (FIG. 6). The inventors also constructed pIG121-7 in which the 2.3-kb EcoRI-HindIII fragment in pIG121-6 inserted in reverse orientation into pIG121-3. The plasmid pIG121-7 demonstrated GUS activity similar to that of the pIG121-3 and pIG121-5. These results suggested that the enhancer elements may be involved in the maximal GUS expression, with enhancement being orientation-dependent.

The GUS reporter gene under the control of the OsPSK 5'-upstream region yielded GUS activity approximately 2 to 5 times higher than that obtained with the GUS gene driven by the CaMV 35S promoter in the transformed Oc cells, suggesting that it contains an efficient promoter for regulating the constitutive expression of a foreign gene in transformed rice Oc culture cells.

Influence of Exogenous Auxin and Cytokinin

Figure 7:
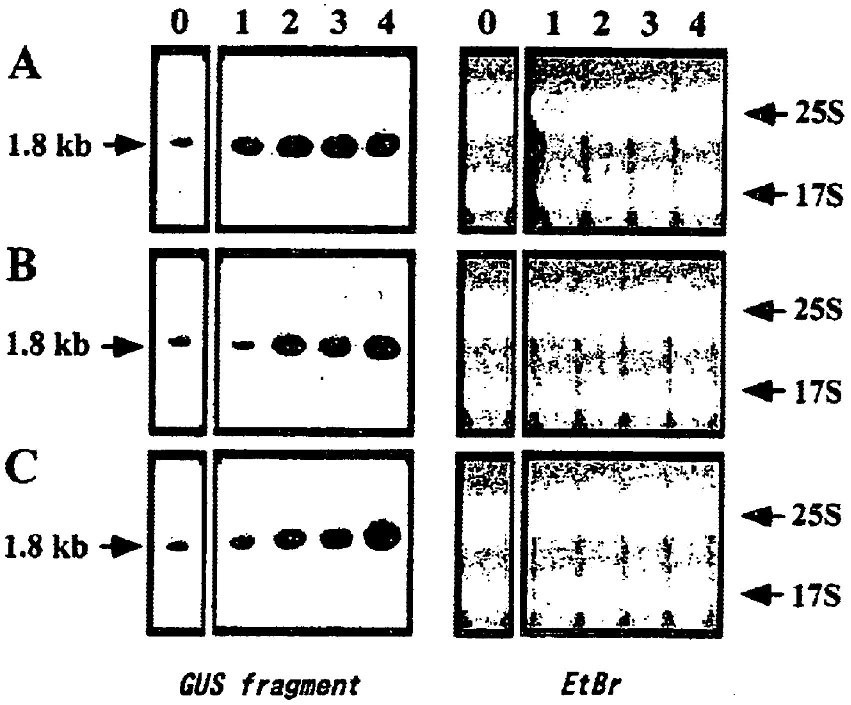
FIG. 7 is a photograph showing regulation of OsPSK::GUS gene by auxin and cytokinin.

The inventors performed RNA blot analyses to investigate how exogenous phytohormones affect the expression of OsPSK::GUS gene in transformed Oc cells. Exogenous auxin (1 mg/l of 2,4-D) and/or cytokinin (1 mg/l of 6-BA) were added into MS media to treat Oc cells transformed with the plasmid pIG121-4. Total RNA was isolated from the various samples and subjected to Northern blot analysis. Exogenous auxin and cytokinin regulation of the OsPSK promoter is shown in FIG. 7. In FIG. 7, steady-state gusA mRNA levels in transformed Oc cells harboring pIG121-4 were examined by Northern blotting (left panel) and ribosomal RNA levels were examined by ethidium bromide staining (right panel). The transformed Oc cells were harvested 0 (lane 0), 12 (lane 1), 24 (lane 2), 48 (lane 3), and 72 h (lane 4) after auxin and/or cytokinin treatment. Total RNA was extracted from each sample and 20 $\mu$g was loaded into each lane. FIG. 7 shows the result of hybridization with the radio-labeled Xba I-Sac I fragment of pIG121 which contains the GUS coding region. FIG. 7A shows the result of MS medium supplemented with 2 mg/l 2,4-D, and the level of GUS mRNA increased significantly at 12 h after the onset of 2,4-D treatment, and reached a maximum level by 48 h (FIG. 7A). FIG. 7B shows the result of MS medium supplemented with 2 mg/l 6-BA and the expression of OsPSK::GUS gene was also reinforced by 6-BA 24 h after treatment, although decrease of GUS transcripts was apparent at 48 h (FIG. 7B). FIG. 7C shows the result of MS medium supplemented with 1 mg/l 2,4-D and 1 mg/l 6-BA. The 2,4-D treatment combined with 6-BA resulted in a consistent increase in the mRNA level throughout the treatment period (FIG. 7C). These results suggested that both exogenous auxin and exogenous cytokinin may enhance the expression of OsPSK in Oc culture cells.

The inventors previously isolated OsPSK cDNA from rice Oc culture cells (Yang et al., 1999). Gain-of-function and loss-of-function studies proved that OsPSK cDNA encodes the precursor of PSK-α, a peptide growth factor identified from plants. In the present investigation, the inventors identified and characterized the OsPSK gene in rice. Southern blotting analyses revealed OsPSK to be a single-copy gene (FIG. 1), consisting of two exons identical to the cDNA sequence, and a large intron (FIG. 2) conserved GT-AG intron border sequence. The first exon contains the 5' non-coding region and a coding region for about half of the PP-PSK (preprophytosulfokine) including the 22 amino acid $NH_2$-terminal hydrophobic region that presumably acts a signal peptide (von Heijne, 1986). No signals that might cause retention along the secretory pathway (Nakai and Kanehisa, 1992) were detected in the sequence of PP-PSK, indicating that the protein may be extracellular and its active form, PSK-α, could therefore act as the ligand for its receptor. The second exon consists of the 3' non-coding region and a coding region within which the 5-amino acid PSK-α sequence occurs only once, close to the COOH-terminus.

Rice Oc cells (Baba et al., 1986) can be simply maintained in/on MS medium (Murashige and Skoog, 1962) supplemented with 1 mg/l 2,4-D with dilution at regular intervals of 2 weeks. The inventors have previously shown that they can serve as an excellent starting material to study the synthesis and physiological function of PSK-α (Yang et al., 1999; Yang et al., 2000a). In the present study, the inventors constructed plasmids with the 5' upstream regions of the OsPSK gene fused to the Intron-GUS reporter gene (Ohta et al., 1990) with a modified intron of the castor bean catalase gene within its N-terminal GUS coding sequence. When placed under the control of the CaMV 35S promoter, the Intron-GUS reporter gene expresses GUS activity with a similar level and pattern as obtained with the original GUS reporter gene in tobacco cells but not in Agrobacterium cells (Ohta et al., 1990). Furthermore, a significant stimulating effect on GUS synthesis by the intron has been observed in rice cells (Tanaka et al., 1991), indicating that the Intron-GUS reporter gene is useful to monitor expression of foreign genes in rice cells. On fusing various lengths of the 5' upstream region of the OsPSK gene, the minimum length of the OsPSK 5'-upstream sequence required for the expression of maximal GUS activity was here found to be a region 1.9 kb upstream of the transcription start site (FIG. 3). This region is approximately 5 times more active than the CaMV 35S promoter in transformed Oc cells, suggesting that it contains an efficient promoter for regulating the constitutive expression of a foreign gene in transformed Oc culture cells.

Within the 5'-upstream region of the OsPSK gene, several known motifs or regulatory elements exist (FIG. 3). One of the most notable features of the OsPSK promoter is the presence of three CCAAT-boxes, which interact with CCAAT/enhancer-binding protein (Ryden and Beeemon, 1989). Furthermore, the inventors identified three SSREs, cis-acting components within the promoter of several human genes expressed in endothelial cells such as those for the platelet-derived growth factor β chain and transforming growth factor β 1 (Resnick et al., 1993). They interact with DNA binding proteins and are necessary for fluid shear-stress responsiveness. Deletion of the region containing these regulatory elements resulted in rather low GUS expression (FIG. 6), suggesting that the SSREs may be actually involved in OsPSK expression. In addition, three E-boxes were found in the 5'-end region of OsPSK. The E-box, with a consensus sequence 5'-CANNTG-3', known as to be a recognition site for a class of transcription factors (basic region/helix-loop-helix proteins), can form homo- and hetero-dimers to exert regulatory function (Pabo, 1992). It is a variation of the G-box (5'-CACGTG-3'; Li and Capetanaki, 1994), elements of which comprise a family of cis-acting sequences that have been shown to be involved in the regulation of gene expression in response to variety of factors in plants as well as in animals (Baker et al., 1994; Dolferus et al., 1994). PSK-α promotes the growth and increase the chlorophyll content of Arabidopsis seedlings under high night-time temperature conditions Yamakawa et al., 1999), suggesting that the E-box conserved in the PSK-α precursor gene may have regulatory functions in the response to environmental stress.

Interestingly, an 8-nucleotide enhancer core-like motif, GTGGAAAG, exists in the 5'-upstream region of OsPSK (FIG. 3). This sequence is the most common among known viral enhancers and dramatically increases the transcriptional activity of certain genes (Weiher et al., 1983). It is also present in the 5'-upstream region of the human ornithine transcarbamylase gene (Hata et al., 1987) and the available findings suggest that the enhancer sequence is universally conserved from viruses to eukaryocytes. The 1.9-kb 5'-upstream region of the OsPSK gene containing the enhancer core-like motif was here shown to be necessary and efficient for maximal-level GUS expression, and that this region was even more active than the CaMV 35S promoter in transformed rice Oc cells (FIG. 5). The enhancer core-like motif in the OsPSK gene may have some functional role in the high-level expression of the OsPSK::GUS gene, this being dependent on the orientation.

When explanted into culture, many plant tissues dedifferentiate and resume division to form proliferating calli. Induction of cell division and subsequent callus formation normally require the simultaneous presence of both auxin and cytokinin. Hence, cell proliferation could be a direct response to auxin and cytokinin or an indirect response caused by PSK-α under their control. In suspension-cultured asparagus mesophyll cells, PSK-α can be produced only when both 1-naphthalene acetic acid and 6-BA are present in the medium. No significant amount of PSK-α is produced if either of these plant hormones is eliminated from the medium, suggesting that both auxin and cytokinin are normally required for the production of PSK-α (Matsubayashi et al., 1999a). Here, the inventors could show that both exogenous auxin and exogenous cytokinin reinforce the expression of OsPSK::GUS in transformed Oc cells (FIG. 7). However, because exogenous hormones may not reflect the endogenous modulation of hormone levels, many more experiments remain to be done before drawing a final conclusion.

According to this invention, a novel promoter sequence derived from phytosulfokine precursor was provided. The potency of this promoter to activate expression of a structural gene was higher than cauliflower mozaic virus 35S promoter.

References

Akama, K., Shiraishi, H., Ohta, S., Nakamura, K., Okada, K. and Shimura, Y. 1992. Efficient transformation of *Arabidopsis thaliana*: comparison of the efficiencies with various organs, plant ecotype and Agrobacterium strains. Plant Cell Rep. 12:7–11.

Allen, R. D., Bernier, F., Lessard, P. and Beachy, R. N. 1989. Nuclear factors interact with a soybean β-conglycinin enhancer. Plant Cell 1: 623–631.

Baba, A., Hasezawa, S. and Syono, K. 1986. Cultivation of rice protoplasts and their transformation mediated by Agrobacterium spheroplasts. Plant Cell Physiol. 27:463–471.

Baker, S. S., Wilhelm, K. S. and Thomashow, M. F. 1994. The 5'-region of *Arabidopsis thaliana* cor15a has cis-acting elements that confer cold-, drought-, and ABA-regulated gene expression. Plant Mol. Biol. 24:701–713.

Bisseling, T. 1999. The role of plant peptides in intercellular signalling. Curr. Opin. Plant Biol. 2:365–368.

Bradford, M. M. 1976. A rapid and sensitive method for the quantification of microgram quantities of protein utilizing the principle of protein-dye binding. Anal. Biochem. 72:248–254.

Chomczynski, P. 1993. A reagent for the single-step simultaneous isolation of RNA, DNA and proteins from cell and tissue samples. BioTechniques 15:532–536.

Dolferus, R., Jacobs, M., Peacock, W. J. and Dennis, E. S. 1994. Differential interactions of promoter elements in stress responses of the Arabidopsis Adh gene. Plant Physiol. 105:1075–1087.

Fletcher, J. C., Brand, U., Running, M. P., Simon, R. and Meyerowitz, E. M. 1999. Signaling of cell fate decisions by CLAVATA3 in Arabidopsis shoot meristems. Science 283:1911–1914.

Franssen, H. J. 1998. Plants embrace a stepchild: the discovery of peptide growth regulators. Curr. Opin. Plant Biol. 1:384–387.

Hanai, H., Matsuno, T., Yamamoto, M., Matsubayashi, Y., Kamada, H. and Sakagami, Y. 2000a. A secreted peptide growth factor, phytosulfokine, acting as a stimulatory factor of carrot somatic embryo formation. Plant Cell Physiol. 41: 27–32.

Hanai, H., Nakayama, D., Yang, H., Matsubayashi, Y., Hirota, Y. and Sakagami, Y. 2000b. Existence of a plant tyrosylprotein sulfotransferase: novel plant enzyme catalyzing tyrosine O-sulfation of preprophytosulfokine variants in vivtro. FEBS Lett. 470:97–101.

Hata A, Tsuzuki T, Shimada K, Takiguchi M, Mori M. and Matsuda I 1986. Isolation and characterization of the human ornithine transcarbamylase gene: structure of the 5'-end region. J. Biochem. 100:717–725.

Huttner, W. B. 1984. Determination and occurrence of tyrosine O-Sulfate in protein. Meth. Enzymol. 107:200–223.

Jefferson, R. A., Kavanagh, T. A. and Bevan, M. W. 1987. GUS fusion: β-glucuronidase as a sensitive and versatile gene fusion marker in higher plants. EMBO J. 6:3901–3907.

Jung, L. J. and Scheller, R. H. 1991. Peptide processing and targeting in the neuronal secretory pathway. Science 251:1330–1335.

Kobayashi, T., Eun, C.-H., Hanai, H., Matsubayashi, Y., Sakagami, Y. and Kamada, H. 1999. Phytosulfokine-α, a peptidyl plant growth factor, stimulates cell division that leads to somatic embryogenesis in carrot. J. Exp. Bot. 50:1123–1128.

Li, H. and Capetanaki, Y. 1994. An E box in the design promoter cooperates with the E box and MEF-2 sites of a distal enhancer to direct muscle-specific transcription. EMBO J. 13:3580–3589.

McGurl, B., Pearce, G., Orozco-Cardenas, M. and Ryan, C. A. 1992. Structure, expression, and antisense inhibition of the systemin precursor gene. Science 255: 1570–1573.

Matsubayashi, Y. and Sakagami, Y. 1996. Phytosulfokine, sulfated peptides that induced the proliferation of single mesophyll cells of *Asparagus officinalis* L. Proc. Natl. Acad. Sci. USA 93:7623–7627.

Matsubayashi, Y., Hanai, H., Hara, O. and Sakagami, Y. 1996. Active fragments and analogs of the plant growth factor, Phytosulfokine: structure-activity relationships. Biochem. Biophys. Res. Commun. 225:209–214.

Matsubayashi, Y., Takagi, L., and Sakagami, Y. 1997. Phytosulfokine-α, a sulfated pentapeptide, stimulates the proliferation of rice cells by means of specific high- and low-affinity binding sites. Proc. Natl. Acad. Sci. USA 94: 13357–13362.

Matsubayashi, Y., Morita, A., Matsunaga, E., Furuya, A., Hanai, N. and Sakagami, Y. 1999a. Physiological relationships between auxin, cytokinin, and a peptide growth factor, phytosulfokine-α, in stimulation of asparagus cell proliferation. Planta 207:559–565.

Matsubayashi, Y., Takagi, L., Omura, N., Morita, A. and Sakagami, Y. 1999b. The endogenous sulfated pentapeptide, phytosulfokine-α, stimulates tracheary element differentiation of isolated mesophyll cells of *Zinnia elegans*. Plant Physiol. 120:1043–1048.

Matsubayashi, Y. and Sakagami, Y. 1999. Characterization of specific binding sites for an endogenous sulfated pentapeptide, phytosulfokine-α, in the plasma membrane fraction derived from *Oryza sativa* L. Eur. J. Biochem. 262:666–671.

Murashige, T. and Skoog, F. 1962. A revised medium for rapid growth and bioassay with tobacco tissue cultures. Physiol. Plant. 15:473–497.

Murry, M. G. and Thompson, W. F. 1980. Rapid isolation of high molecular weight plant DNA. Nucl. Acids Res. 8:4321–4325.

Nakai, K. and Kanehisa, M. 1992. A knowledge base for predicting protein localization sites in eukaryotic cells. Genomics 14:897–911.

Ohta, S., Mita, S., Hattori, T. and Nakamura, K. 1990. Construction and expression in tobacco of a β-glucuronidase (GUS) reporter gene containing an intron within the coding sequence. Plant Cell Physiol. 31:805–813.

Pabo, C. O. 1992. Transcription factors: structural families and principles of DNA recognition. Annu. Rev. Biochem. 61:1053–1095.

Resnick, N., Collins, T., Atkinson, W., Bomthron, D. T., Dewey, C. F. Jr. and Gimbrone, M. R. Jr. 1993. Platelet-derived growth factor β chain promoter contains a cis-acting fluid shear-stress responsive element. Proc. Natl. Acad. Sci. USA 90:4591–4595.

Ryden, T. A. and Beemon, K. 1989. Avian retroviral long terminal repeats bind CCAAT/enhancer-binding protein. Mol. Cell Biol. 9:1155–1164.

Sambrook, J., Fritsch, E. F. and Maniatis, T. 1989. Molecular Cloning: A Laboratory Manual, 2nd ed., Cold Spring Harbor Laboratory Press, Cold Spring Harbor, N.Y.

Schaller, A. 1999. Oligopeptide signalling and the action of systemin. Plant Mol. Biol. 40:763–769.

Tanaka, A., Mita, S., Ohta, S., Kyozuka, J., Shimamoto, K. and Nakamura, K. 1991. Enhancement of foreign gene expression by a dicot intron in rice but not in tobacco is correlated with an increased level of mRNA an efficient splicing of the intron. Nucl. Acids Res. 18:6767–6770.

von Heijne, G. 1986. A new method for predicting signal sequence cleavage sites. Nucl. Acids Res. 14:4683–4690.

Weither, H., Konig, M. and Gruss, P. 1983. Multiple point mutations affecting the simian virus 40 enhancer. Science 219:626–631.

Yamakawa, S., Matsubayashi, Y., Sakagami, Y., Kamada, H. and Satoh, S. 1999. Promotive effects of the peptidyl plant growth factor, phytosulfokine-α, on the growth and chlorophyll content of Arabidopsis seedlings under high night-time temperature conditions. Biosci. Biotechnol. Biochem. 63:2240–2243.

Yang, H., Matsubayashi, Y., Nakamura, K. and Sakagami, Y. 1999. *Oryza sativa* PSK encodes a precursor of phytosulfokine-α, a sulfated peptide growth factor found in plants. Proc. Natl. Acad. Sci. USA 96:13560–13565.

Yang, H., Morita, A., Matsubayashi, Y., Nakamura, K. and Sakagami, Y. 2000a. Rapid and efficient Agrobacterium infection-mediated transient gene expression in rice Oc cells and its application for expression and antisense suppression of OsPSK cDNA for a precursor to phytosulfokine-α, a peptide plant growth factor. Plant Cell Physiol. 41:(in press)

Yang, H., Matsubayashi, Y., Hanai, H. and Sakagami, Y. 2000b. Phytosulfokine-α, a peptide growth factors found in higher plant: its structure, functions, precursor and receptors. Plant Cell Physiol. 41:(in press)

What is claimed is:

1. An isolated promoter comprising SEQ ID NO: 1.

2. A plasmid comprising the promoter of claim 1.

3. A transgenic plant cell comprising the promoter of claim 1.

4. A transgenic plant comprising the promoter of claim 1.

5. An isolated promoter comprising SEQ ID NO: 2.

6. A plasmid comprising the promoter of claim 5.

7. A transgenic plant cell comprising the promoter of claim 5.

8. A transgenic plant comprising the promoter of claim 5.

9. An isolated promoter comprising SEQ ID NO: 3.

10. A plasmid comprising the promoter of claim 9.

11. A transgenic plant cell comprising the promoter of claim 9.

12. A transgenic plant comprising the promoter of claim 9.

13. A method for activating expression of an exogenous structural gene or an endogenous structural gene wherein said method comprises incorporating the promoter according to claim 1, claim 5, or claim 9 upstream of said structural gene.

* * * * *